US009490144B2

(12) United States Patent
Ogihara et al.

(10) Patent No.: US 9,490,144 B2
(45) Date of Patent: Nov. 8, 2016

(54) QUATERNARY AMMONIUM SALT COMPOUND, COMPOSITION FOR FORMING A RESIST UNDER LAYER FILM, AND PATTERNING PROCESS

(71) Applicant: SHIN-ETSU CHEMICAL CO., LTD., Tokyo (JP)

(72) Inventors: Tsutomu Ogihara, Jyoetsu (JP); Takeru Watanabe, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/680,581

(22) Filed: Apr. 7, 2015

(65) Prior Publication Data

US 2015/0357204 A1    Dec. 10, 2015

(30) Foreign Application Priority Data

Jun. 4, 2014    (JP) .................................. 2014-115506

(51) Int. Cl.
| | |
|---|---|
| H01L 21/3213 | (2006.01) |
| C07C 211/63 | (2006.01) |
| C07C 219/28 | (2006.01) |
| C07C 229/38 | (2006.01) |
| C08K 5/19 | (2006.01) |
| H01L 21/311 | (2006.01) |
| C07C 219/14 | (2006.01) |
| C07C 229/12 | (2006.01) |

(52) U.S. Cl.
CPC ....... *H01L 21/32135* (2013.01); *C07C 211/63* (2013.01); *C07C 219/14* (2013.01); *C07C 219/28* (2013.01); *C07C 229/12* (2013.01); *C07C 229/38* (2013.01); *C08K 5/19* (2013.01); *H01L 21/31116* (2013.01); *H01L 21/31144* (2013.01); *H01L 21/32139* (2013.01); *C07C 2103/24* (2013.01)

(58) Field of Classification Search
CPC .................. H01L 21/32135; H01L 121/31144; C07C 211/63; C07C 219/28; C07C 229/38; C08K 5/19
See application file for complete search history.

(56) References Cited

U.S. PATENT DOCUMENTS

| | | | |
|---|---|---|---|
| 5,632,910 A | 5/1997 | Nagayama et al. | |
| 2007/0238300 A1 | 10/2007 | Ogihara et al. | |
| 2008/0161267 A1* | 7/2008 | Taylor | A61K 31/66 514/58 |
| 2009/0011366 A1 | 1/2009 | Tsubaki et al. | |
| 2009/0136869 A1 | 5/2009 | Ogihara et al. | |
| 2010/0040972 A1 | 2/2010 | Tarutani et al. | |

FOREIGN PATENT DOCUMENTS

| | | | |
|---|---|---|---|
| CN | 101906049 | 12/2010 | |
| JP | H07-181688 A | 7/1995 | |
| JP | H07-183194 A | 7/1995 | |
| JP | 2005-520354 A | 7/2005 | |
| JP | 2007-302873 A | 11/2007 | |
| JP | 2008-281974 A | 11/2008 | |
| JP | 2008-281980 A | 11/2008 | |
| JP | 2009-053657 A | 3/2009 | |
| JP | 2009-126940 A | 6/2009 | |
| JP | 4716037 B2 | 7/2011 | |
| JP | 2014-056122 * | 3/2014 | ............ G03F 7/029 |
| WO | 2004/007192 A1 | 1/2004 | |

OTHER PUBLICATIONS

Machine translation of JP 2014-056122. Mar. 2014.*
Terry et al. Physiologically Relevant Concentrations of NaCl and KCl Increase DNA Photocleavage by N-Substituted 9-Aminomethylanthracene Dye. Biochemistry 2011, 50, 10375-10389.*
Balan et al. An Anthracene-Appended B-Cyclodextrin-Based Dyad: Study of Self-Assembly and Photoinduced Electron-Transfer Processes. Chem. Eur. J. 2007, 13, 5173-5185.*
Apr. 13, 2016 Office Action issued in Taiwanese Patent Application No. 104117711.

* cited by examiner

*Primary Examiner* — John Uselding
(74) *Attorney, Agent, or Firm* — Oliff LC

(57) ABSTRACT

A quaternary ammonium salt compound is represented by the following formula (A-1), (A-1)

$$\left[ R^2-\overset{R^1}{\underset{R^3}{\overset{\oplus}{N}}}-R^4-\text{(anthracenyl)} \right] A^\ominus$$

wherein, $R^1$, $R^2$, and $R^3$ each represent an alkyl group, an alkenyl group, an aryl group, or an aralkyl group, a part or all of hydrogen atoms in these groups may be substituted by a hydroxyl group(s), an alkoxy group(s), or a halogen atom(s), and these groups may include one or more of a carbonyl group and an ester bond; $R^4$ represents a single bond, an alkylene group, an alkenylene group, an arylene group, or an aralkylene group, a part or all of hydrogen atoms in these groups may be substituted by an alkoxy group(s) or a halogen atom(s), and these groups may include one or more of an ether bond, a carbonyl group, an ester bond, and an amide bond; and $A^-$ represents a non-nucleophilic counter ion.

20 Claims, No Drawings

QUATERNARY AMMONIUM SALT COMPOUND, COMPOSITION FOR FORMING A RESIST UNDER LAYER FILM, AND PATTERNING PROCESS

BACKGROUND OF THE INVENTION

1. Field of the Invention

The present invention relates to a quaternary ammonium salt compound, a composition for forming a resist under layer film containing the same, and a patterning process using the same.

2. Description of the Related Art

In 1980s, photo-exposure using a g-beam (436 nm) or an i-beam (365 nm) of a mercury lamp as a light source had been widely used in the resist patterning. As a means for finer patterning, shifting to a exposure light having shorter wavelength was assumed to be effective, so that, for the mass production process of DRAM (Dynamic Random Access Memory) with 64 MB (work size of 0.25 μm or less) in 1990s and later ones, a KrF excimer laser (248 nm), whose wavelength is shorter than the i-beam (365 nm), had been used in place of the i-beam as the exposure light source. However, for production of DRAM with integration of 256 MB and 1 GB or higher requiring further finer processing technologies (work size of 0.2 μm or less), a light source with a shorter wavelength was required, and thus, a photolithography using an ArF excimer laser (193 nm) has been investigated seriously over a decade.

It was expected at first that the ArF lithography would be applied to the fabrication of 180 nm-node devices. However, the KrF excimer lithography survived to the mass production of 130 nm-node devices, so that a full-fledged application of the ArF lithography started from the 90 nm-node. Furthermore, mass production of the 65 nm-node devices is now underway by combining the ArF lithography with a lens having an increased numerical aperture (NA) of 0.9. For the next 45 nm-node devices, further shortening the wavelength of exposure light is progressing, and the $F_2$ lithography with 157 nm wavelength became a candidate.

However, there are many problems in the $F_2$ lithography: cost-up of a scanner due to use of the large quantities of the expensive $CaF_2$ single crystal for a projection lens; extremely poor durability of a soft pellicle, which leads to change of an optical system due to introduction of a hard pellicle; decrease in etching resistance of a resist film, and so forth. Because of these problems, development of the $F_2$ lithography was suspended, and the ArF immersion lithography was introduced.

In the ArF immersion lithography, water having refractive index of 1.44 is introduced between a projection lens and a wafer by a partial fill method, thereby enabling high speed scanning, and thus, mass production of the 45 nm-node devices is now underway by using a lens with a NA of 1.3.

For the 32 nm-node lithography, lithography with an Extreme-ultraviolet beam (EUV) of 13.5 nm wavelength is considered to be a candidate. Problems to be solved in the EUV lithography are to obtain a higher output power of the laser, a higher sensitivity of the resist film, a higher resolution, a lower line edge roughness (LER), a non-defect MoSi laminate mask, a lower aberration of the reflective mirror, and so forth; and thus, there are innumerable problems to be solved.

Development of the immersion lithography with a high refractive index, another candidate for the 32 nm-node, was suspended because transmittance of LUAG, a candidate for a high refractive index lens, is low, and refractive index of the liquid could not reach an aimed value of 1.8.

As mentioned above, in the photo-exposure used as a general technology, resolution based on the wavelength of the light source is approaching to its inherent limit. Thus, in recent years, patterning through negative tone by organic solvent development that can form a very fine hole pattern, which is not achievable by conventional patterning through positive tone by alkaline development, attracted attention again. This is a process for forming a negative pattern by using a positive resist composition featuring a high resolution by organic solvent development. Furthermore, an attempt to double a resolution by combining two developments, alkaline development and organic solvent development, is under study (Patent Documents 1 to 3).

A multilayer resist method is one of the methods for transferring a lithography pattern to a substrate. In this method, an intermediate film (e.g. a silicon-containing resist under layer film) having etching selectivity different from that of a photoresist film, i.e. a resist upper layer film, is interposed between the resist upper layer film and a substrate to be processed, a pattern is formed to the resist upper layer film, and the pattern is then transferred to the resist under layer film by dry etching using the upper layer resist pattern as a dry etching mask, and further the pattern is transferred to the substrate to be processed by dry etching using the resist under layer film as a dry etching mask.

As a material to be used for such a multilayer resist method, a composition for forming a silicon-containing film has been well known. For example, a silicon-containing inorganic film formed by a CVD method such as a $SiO_2$ film (Patent Document 4) and a SiON film (Patent Document 5), and a material that can be obtained by spin-coating such as a SOG (spin-on-glass) film (Patent Document 6) and a cross-linkable silsesquioxane film (Patent Document 7) may be mentioned.

PRIOR ART DOCUMENTS

Patent Documents

Patent Document 1: Japanese Patent Laid-Open Publication No. 2008-281974
Patent Document 2: Japanese Patent Laid-Open Publication No. 2008-281980
Patent Document 3: Japanese Patent Laid-Open Publication No. 2009-053657
Patent Document 4: Japanese Patent Laid-Open Publication No. H07-183194
Patent Document 5: Japanese Patent Laid-Open Publication No. H07-181688
Patent Document 6: Japanese Patent Laid-Open Publication No. 2007-302873
Patent Document 7: Japanese Patent Laid-Open Publication No. 2005-520354

SUMMARY OF THE INVENTION

The present inventors have earnestly investigated on lithography characteristics and stability of a composition for forming a silicon-containing resist under layer film until now, and provided a composition for forming a silicon-containing resist under layer film containing a thermal crosslinking accelerator as disclosed in Japanese Patent No. 4716037, thereby a silicon-containing resist under layer film excellent in etching selectivity and storage stability could be provided.

However, miniaturization of a semiconductor apparatus not only progresses in horizontal direction for thinning the line width of the substrate pattern, but also progresses toward lamination in vertical direction, i.e. high densification in three-dimension, so that processing in vertical direction becomes important in the process for processing a substrate. Thus, enough film thickness is required for a coating film used as an etching mask, and hard mask for etching becomes necessary also for a rough design pattern, which has been considered not to need a hard mask.

The present invention has been done to solve the above-mentioned problems, and an object thereof is to provide a quaternary ammonium salt compound that can suppress reflection particularly in KrF exposure process and improve a pattern profile, compared with a case using the conventional silicon-containing resist under layer film, when the quaternary ammonium salt compound is added to a composition for forming a resist under layer film.

To solve the above-mentioned problems, the present invention provides a quaternary ammonium salt compound represented by the following formula (A-1),

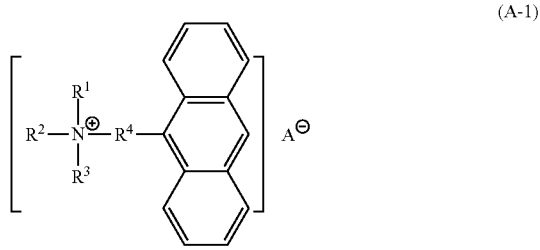

(A-1)

wherein, $R^1$, $R^2$, and $R^3$ each represent a linear, branched or cyclic alkyl group or alkenyl group having 1 to 12 carbon atoms, an aryl group having 6 to 20 carbon atoms, or an aralkyl group having 7 to 12 carbon atoms, a part or all of hydrogen atoms in these groups may be substituted by a hydroxyl group(s), an alkoxy group(s), or a halogen atom(s), and these groups may include one or more of a carbonyl group and an ester bond; $R^4$ represents a single bond, a linear, branched or cyclic alkylene group or alkenylene group having 1 to 12 carbon atoms, an arylene group having 6 to 20 carbon atoms, or an aralkylene group having 7 to 12 carbon atoms, a part or all of hydrogen atoms in these groups may be substituted by an alkoxy group(s) or a halogen atom(s), and these groups may include one or more of an ether bond, a carbonyl group, an ester bond, and an amide bond; and $A^-$ represents a non-nucleophilic counter ion.

By adding such a quaternary ammonium salt compound to a composition for forming a resist under layer film, a resist under layer film which can suppress reflection particularly in KrF exposure process, and has excellent adhesiveness to a resist pattern formed thereon can be formed.

Also, the present invention provides a composition for forming a resist under layer film which includes the quaternary ammonium salt compound and a polysiloxane.

Such a composition for forming a resist under layer film can form a resist under layer film which can suppress reflection particularly in KrF exposure process, and has excellent adhesiveness to a resist pattern formed thereon and excellent dry etching selectivity between a resist pattern formed thereon and an organic under layer film or the like formed thereunder.

The polysiloxane preferably includes one or more members selected from a compound represented by the following formula (B-1), a hydrolysate of the compound, a condensate of the compound, and a hydrolysis condensate of the compound,

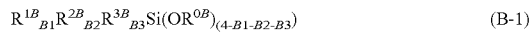

$$R^{1B}{}_{B1}R^{2B}{}_{B2}R^{3B}{}_{B3}Si(OR^{OB})_{(4-B1-B2-B3)} \quad \text{(B-1)}$$

wherein, $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \le B1+B2+B3 \le 3$.

When the composition for forming a resist under layer film includes such a polysiloxane, the above-mentioned adhesiveness and dry etching selectivity are further excellent.

Furthermore, the present invention provides a patterning process which includes the steps of: forming an organic under layer film on a body to be processed by using a coating type organic under layer film material; forming a resist under layer film on the organic under layer film by using the above-mentioned composition for forming a resist under layer film; forming a resist pattern on the resist under layer film; transferring the pattern to the resist under layer film by dry etching using the resist pattern as a mask; transferring the pattern to the organic under layer film by dry etching using the resist under layer film to which the pattern has been transferred as a mask; and further transferring the pattern to the body to be processed by dry etching using the organic under layer film to which the pattern has been transferred as a mask.

At this time, the coating type organic under layer film material preferably contains an anthracene skeleton.

By forming the above-mentioned resist under layer film on the organic under layer film containing an anthracene skeleton, reflection can be further suppressed.

Also, the present invention provides a patterning process which includes the steps of: forming an organic hard mask mainly comprising carbon on a body to be processed by a CVD method; forming a resist under layer film on the organic hard mask by using the above-mentioned composition for forming a resist under layer film; forming a resist pattern on the resist under layer film; transferring the pattern to the resist under layer film by dry etching using the resist pattern as a mask; transferring the pattern to the organic hard mask by dry etching using the resist under layer film to which the pattern has been transferred as a mask; and further transferring the pattern to the body to be processed by dry etching using the organic hard mask to which the pattern has been transferred as a mask.

In this way, the patterning process by the three-layer resist method using the composition for forming a resist under layer film of the present invention enables a fine pattern to be formed on a substrate with high precision.

At this time, the body to be processed is preferably a semiconductor apparatus substrate or a material in which any of a metal film, a metal carbide film, a metal oxide film, a metal nitride film, a metal oxycarbide film, and a metal oxynitride film is formed on the semiconductor apparatus substrate.

Moreover, a metal constituting the body to be processed preferably includes silicon, titanium, tungsten, hafnium, zirconium, chromium, germanium, copper, aluminum, indium, gallium, arsenic, palladium, iron, tantalum, iridium, molybdenum, or an alloy thereof.

In this way, the patterning process of the present invention can form a pattern by processing the above-mentioned body to be processed.

As mentioned above, the quaternary ammonium salt compound of the present invention can form a resist under layer film that can suppress reflection particularly in KrF exposure process, and exhibits excellent adhesiveness to a resist pattern formed thereon and high dry etching selectivity to both of the resist pattern formed thereon and an organic under layer film (or an organic hard mask) formed thereunder, by adding the quaternary ammonium salt compound, for example, as a thermal crosslinking accelerator to a composition for forming a resist under layer film containing a polysiloxane. Accordingly, when the formed resist pattern is successively transferred to the resist under layer film and the organic under layer film (or the organic hard mask) by dry etching process, the pattern can be transferred with good pattern profile. In this way, the pattern formed to the upper layer resist can be finally transferred to the body to be processed with high precision.

DETAILED DESCRIPTION OF THE PREFERRED EMBODIMENTS

As mentioned above, it has been desired to develop a thermal crosslinking accelerator that can suppress reflection particularly in KrF exposure process and improve a pattern profile, compared with a case using the conventional silicon-containing resist under layer film, by adding the same to a composition for forming a resist under layer film.

The present inventors earnestly investigated on the above problems and consequently found that the above problems can be solved by adding the quaternary ammonium salt compound of the present invention to a composition for forming a resist under layer film as a thermal crosslinking accelerator, thereby bringing the present invention to completion.

That is, the present invention is a quaternary ammonium salt compound represented by the following formula (A-1),

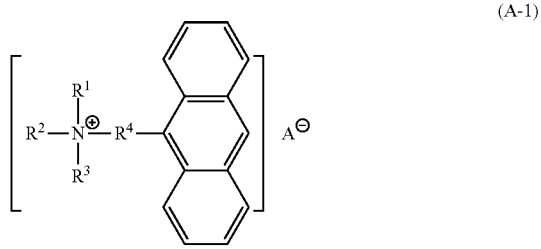

wherein, $R^1$, $R^2$, and $R^3$ each represent a linear, branched or cyclic alkyl group or alkenyl group having 1 to 12 carbon atoms, an aryl group having 6 to 20 carbon atoms, or an aralkyl group having 7 to 12 carbon atoms, a part or all of hydrogen atoms in these groups may be substituted by a hydroxyl group(s), an alkoxy group(s), or a halogen atom(s), and these groups may include one or more of a carbonyl group and an ester bond; $R^4$ represents a single bond, a linear, branched or cyclic alkylene group or alkenylene group having 1 to 12 carbon atoms, an arylene group having 6 to 20 carbon atoms, or an aralkylene group having 7 to 12 carbon atoms, a part or all of hydrogen atoms in these groups may be substituted by an alkoxy group(s) or a halogen atom(s), and these groups may include one or more of an ether bond, a carbonyl group, an ester bond, and an amide bond; and $A^-$ represents a non-nucleophilic counter ion.

Hereinafter, the present invention will be described in detail, but the present invention is not limited thereto.

Herein, "Me" represents a methyl group, "Et" represents an ethyl group, and "Ph" represents a phenyl group.

<Quaternary Ammonium Salt Compound>

The quaternary ammonium salt compound of the present invention is a compound represented by the following formula (A-1) having an anthracene structure, and can be used as a thermal crosslinking accelerator,

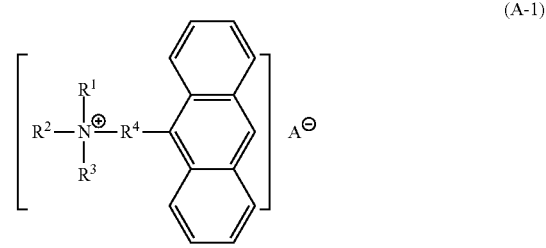

wherein, $R^1$, $R^2$, and $R^3$ each represent a linear, branched or cyclic alkyl group or alkenyl group having 1 to 12 carbon atoms, an aryl group having 6 to 20 carbon atoms, or an aralkyl group having 7 to 12 carbon atoms, a part or all of hydrogen atoms in these groups may be substituted by a hydroxyl group(s), an alkoxy group(s), or a halogen atom(s), and these groups may include one or more of a carbonyl group and an ester bond; $R^4$ represents a single bond, a linear, branched or cyclic alkylene group or alkenylene group having 1 to 12 carbon atoms, an arylene group having 6 to 20 carbon atoms, or an aralkylene group having 7 to 12 carbon atoms, a part or all of hydrogen atoms in these groups may be substituted by an alkoxy group(s) or a halogen atom(s), and these groups may include one or more of an ether bond, a carbonyl group, an ester bond, and an amide bond; and $A^-$ represents a non-nucleophilic counter ion.

In the above formula, $R^1$, $R^2$, and $R^3$ each independently represent a linear, branched or cyclic alkyl group or alkenyl group having 1 to 12 carbon atoms, an aryl group having 6 to 20 carbon atoms, or an aralkyl group having 7 to 12 carbon atoms, a part or all of hydrogen atoms in these groups may be substituted by a hydroxyl group(s), an alkoxy group(s), or a halogen atom(s), and these groups may include one or more of a carbonyl group and an ester bond.

Illustrative examples thereof include methyl group, ethyl group, butyl group, isopropyl group, cyclohexyl group, allyl group, 2-oxopropyl group, 2-oxo-3-butenyl group, phenyl group, naphthyl group, anthracenyl group, tolyl group, anisyl group, benzyl group, methoxybenzyl group, naphthylmethyl group, phenethyl group, 3-phenyl-2-oxopropyl group, 2-methoxyethyl group, 2-[2-methoxyethoxy]ethoxy group, trifluoroethyl group, 2-hydroxyethyl group, 2-hydroxypropyl group, etc.

In the above formula, $R^4$ represents a single bond, a linear, branched or cyclic alkylene group or alkenylene group having 1 to 12 carbon atoms, an arylene group having 6 to 20 carbon atoms, or an aralkylene group having 7 to 12 carbon atoms, a part or all of hydrogen atoms in these groups may be substituted by an alkoxy group(s) or a halogen atom(s), and these groups may include one or more of an ether bond, a carbonyl group, an ester bond, and an amide bond.

Illustrative examples thereof include single bond, methylene group, ethylene group, propylene group, cyclohexanediyl group, propene-1,3-diyl group, 2-butene-1,4-diyl group, 2-oxopropane-1,3-diyl group, 1-oxo-2-propene-1,3-diyl group, etc. Furthermore, other examples include a divalent organic group obtained by removing two hydrogen atoms from a compound selected from benzene, naphthalene, anthracene, toluene, xylene, trimethylbenzene, ethylbenzene, benzaldehyde, acetophenone, ethylmethyl ether, diethyl ether, dipropyl ether, isopropylmethyl ether, 2,2-difluoropropane, 1,1,1-trifluoroethane, anisole, fluorobenzene, ethyl formate, methyl acetate, ethyl acetate, propyl acetate, butyl acetate, methyl propionate, ethyl propionate, propyl propionate, ethyl butyrate, methyl benzoate, ethyl benzoate, propyl benzoate, tolyl benzoate, acetamide, N-methylformamide, N,N-dimethylformamide, N,N-dimethylacetamide, N-methylacetamide, and the like.

In the above formula, A⁻ represents a non-nucleophilic counter ion. Herein, the term of "counter ion" denotes a counter anion of a quaternary ammonium cation. Illustrative examples thereof include hydroxide ion, formate ion, acetate ion, propionate ion, butanoate ion, pentanoate ion, hexanoate ion, heptanoate ion, octanoate ion, nonanoate ion, decanoate ion, oleate ion, stearate ion, linoleate ion, linolenate ion, benzoate ion, p-methylbenzoate ion, p-tert-butylbenzoate ion, phthalate ion, isophthalate ion, terephthalate ion, salicylate ion, trifluoroacetate ion, pentafluoropropionate ion, heptafluorobutanoate ion, monochloroacetate ion, dichloroacetate ion, trichloroacetate ion, fluoride ion, chloride ion, bromide ion, iodide ion, nitrate ion, chlorate ion, perchlorate ion, bromate ion, iodate ion, oxalate ion, malonate ion, methylmalonate ion, ethylmalonate ion, propylmalonate ion, butylmalonate ion, dimethylmalonate ion, diethylmalonate ion, succinate ion, methylsuccinate ion, glutarate ion, adipate ion, itaconate ion, maleate ion, fumarate ion, citraconate ion, citrate ion, carbonate ion, hydrogen carbonate ion, hydrogen sulfate ion, p-toluenesulfate ion, methanesulfonate ion, etc.

Among these, particularly preferable examples include formate ion, acetate ion, propionate ion, butanoate ion, pentanoate ion, hexanoate ion, heptanoate ion, octanoate ion, nonanoate ion, decanoate ion, oleate ion, stearate ion, linoleate ion, linolenate ion, benzoate ion, p-methylbenzoate ion, p-tert-butylbenzoate ion, trifluoroacetate ion, pentafluoropropionate ion, heptafluorobutanoate ion, chloride ion, nitrate ion, oxalate ion, carbonate ion, hydrogen carbonate ion, etc.

Cation portion of the quaternary ammonium salt compound of the present invention represented by the formula (A-1) is represented by the following formula (A-1a),

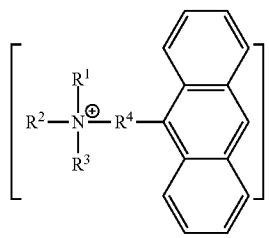

(A-1a)

wherein, R¹, R², R³, and R⁴ have the same meanings as above.

The cation represented by the formula (A-1a) can be exemplified by the following, but not limited thereto.

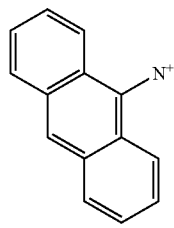 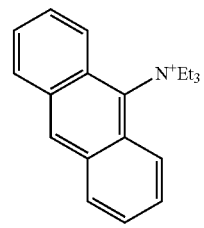

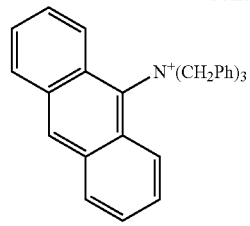

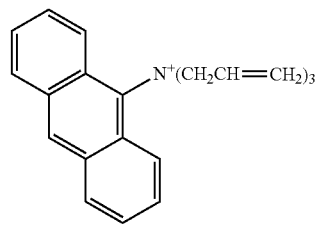

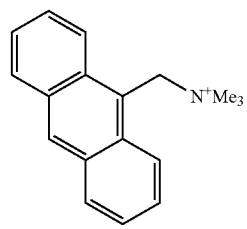 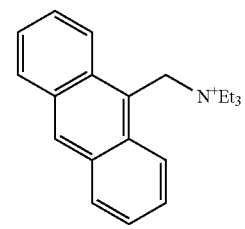

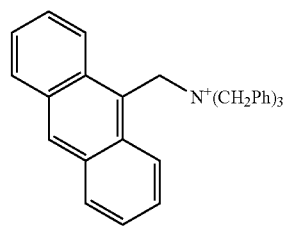

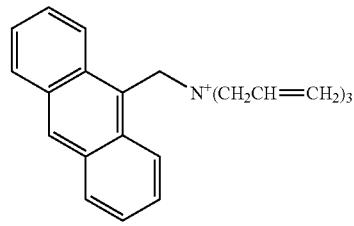

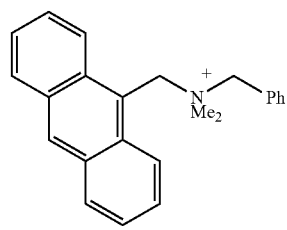

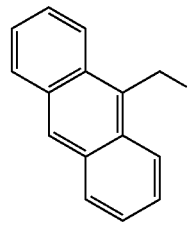 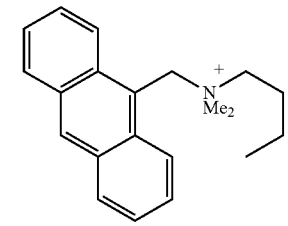

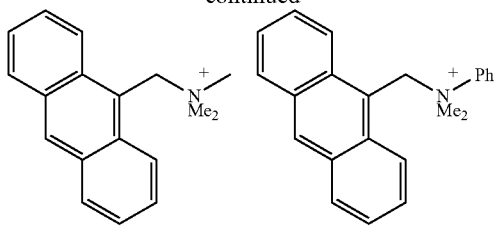
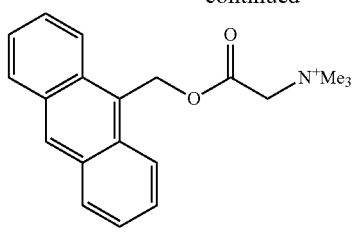
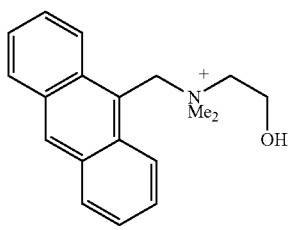
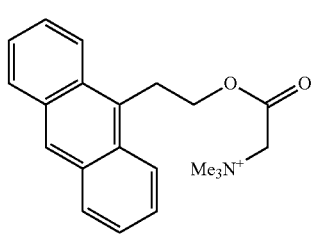
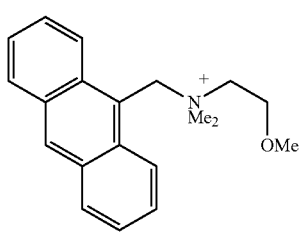
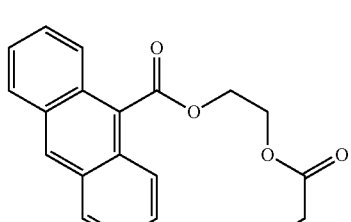
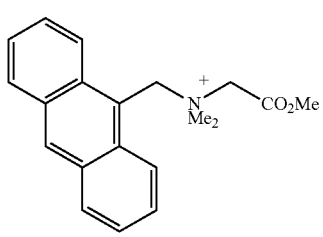
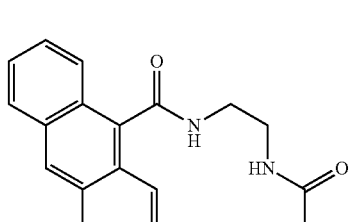
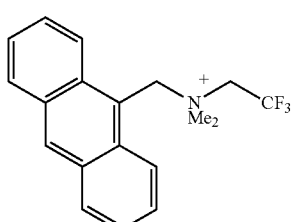
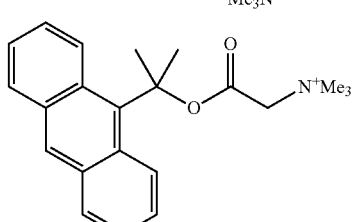
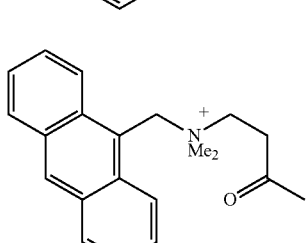
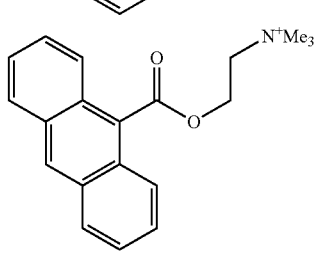
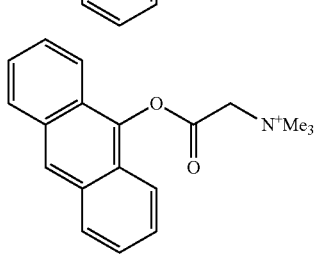
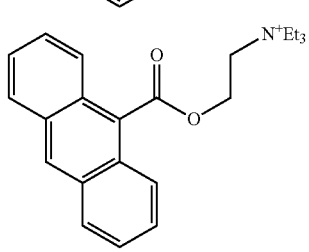

11
-continued
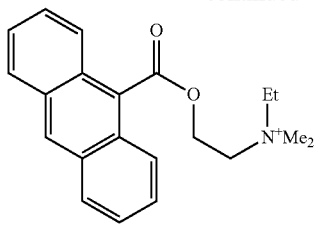
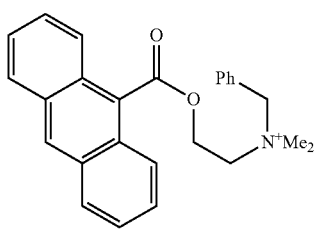
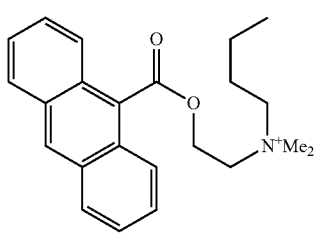
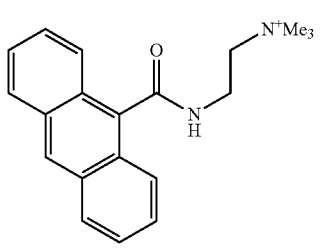
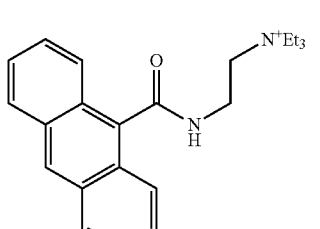
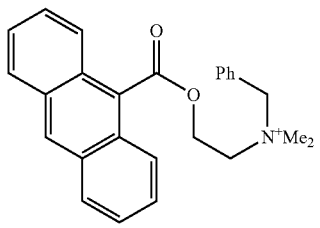
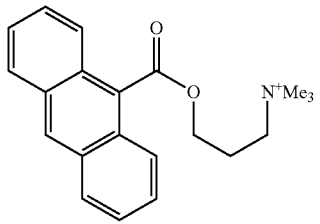
12
-continued
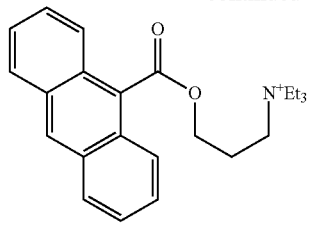
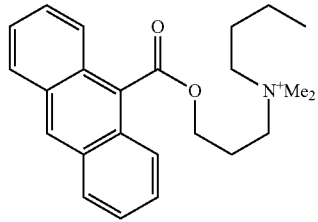
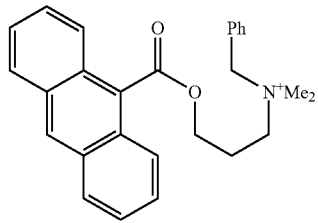
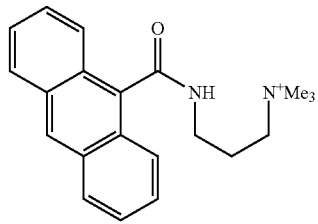
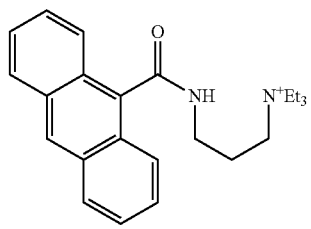
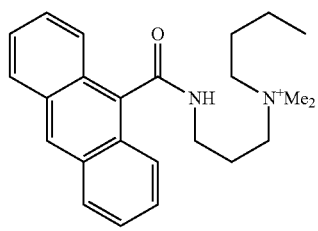
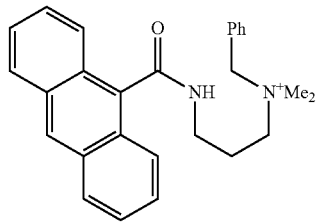

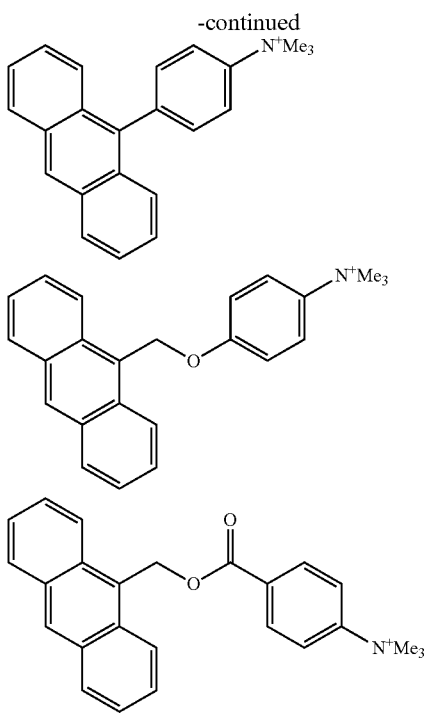

An anthracene containing quaternary ammonium cation represented by the formula (A-1a) is preferably prepared by selecting an optimal method depending on structures. Typical examples include the following two methods: (A) N-alkylation reaction of a tertiary amine compound with an anthracene compound having a leaving group, and (B) condensation reaction of a quaternary ammonium salt compound to be used as a material and an anthracene compound, but is not limited to these methods. In the following, these methods are described in detail.

[Method A]

First, the method A, synthesis of an anthracene containing quaternary ammonium cation represented by the formula (A-1a) by N-alkylation reaction of a tertiary amine compound with an anthracene compound having a leaving group will be described.

Typical chemical equation for the reaction is shown below,

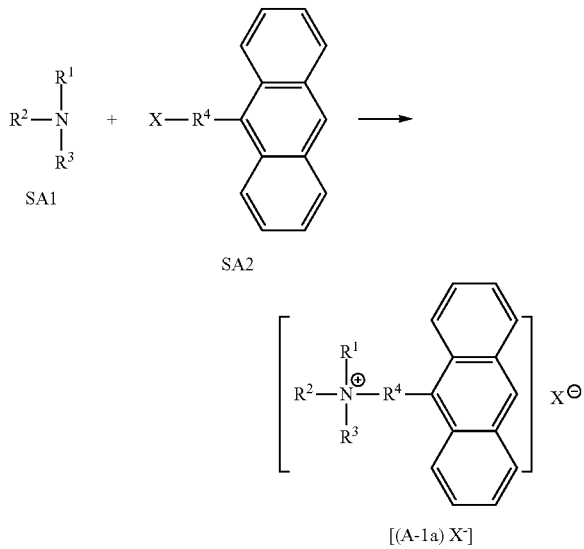

wherein $R^1$, $R^2$, $R^3$, and $R^4$ have the same meanings as above; X represents a leaving group; and $X^-$ represents an ion of the leaving group, which is a counter anion of a quaternary ammonium cation.

Illustrative examples of $R^1$, $R^2$, $R^3$, and $R^4$ include the same as described above.

X represents a leaving group. Illustrative examples thereof include halogen atoms such as a chlorine atom, a bromine atom, and an iodine atom; alkylsulfonyloxy groups such as a methanesulfonyloxy group; and arylsulfonyloxy groups such as a p-toluenesulfonyloxy group.

The amount of the tertiary amine compound (SA1) to be used is desirably in the range of 0.3 to 50 mol, more desirably 0.8 to 10 mol per 1 mol of the anthracene compound having a leaving group (SA2). The reaction is performed in a solvent, or without solvent.

Examples of the solvent include alcohols such as methanol, ethanol, isopropyl alcohol, tert-butyl alcohol, and ethylene glycol; hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform, and 1,2-dichloroethylene; aprotic polar solvents such as N,N-dimethylformamide, N,N-dimethylacetamide, dimethyl sulfoxide, and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. A suitable solvent or solvents may be selected from these, and used alone or in combination with two or more kinds thereof depending on reaction conditions.

The reaction temperature may be selected in the range of −20° C. to 200° C., depending on the desired reaction rate. If the boiling point of the solvent or the tertiary amine compound (SA1) is lower than the reaction temperature, the reaction is preferably performed in an autoclave.

Also, a base may be added to the reaction system for promoting the reaction. Examples of the base to be added include amines such as pyridine, triethylamine, diisopropylethylamine, 4-dimethylaminopyridine, and imidazole; metal alkoxides such as sodium methoxide, sodium ethoxide, and potassium tert-butoxide; carbonates such as sodium carbonate, potassium carbonate, and cesium carbonate; hydroxides such as sodium hydroxide, potassium hydroxide, and tetramethylammonium hydroxide; metal hydrides such as sodium hydride and potassium hydride; organometallic compounds such as butyl lithium and ethyl magnesium bromide; and metal amides such as lithium diisopropyl amide. A suitable base or bases may be selected from these, and used alone or in combination with two or more kinds thereof depending on reaction conditions.

The amount of the base to be used is desirably in the range of 0.3 to 10 mol, more desirably 0.5 to 5 mol per 1 mol of the anthracene compound having a leaving group (SA2).

Also, a catalyst may be added to the reaction system for accelerating the reaction rate. Examples of the catalyst include iodides such as sodium iodide, lithium iodide, and tetrabutylammonium iodide; and bromides such as sodium bromide, lithium bromide, and tetrabutylammonium bromide.

The amount of the catalyst to be added is desirably in the range of 0.001 to 2 mol, more desirably 0.005 to 0.5 mol per 1 mol of the anthracene compound having a leaving group (SA2).

In view of yield, the reaction time is desirably determined by monitoring the reaction process by gas chromatography (GC) or thin-layer chromatography (TLC) so as to bring the reaction to completion. Usually the reaction time is about 0.1 to 100 hours.

After completion of the reaction, a quaternary ammonium salt compound containing an anthracene structure can be obtained by concentrating the reaction mixture. If necessary, the compound may be purified by standard techniques like water-washing, chromatography, and recrystallization. Alternatively, a poor solvent may be added to the reaction solution, thereby the target compound can be directly crystalized and purified from the reaction solvent.

[Method B]

Next, the method B, synthesis of an anthracene containing quaternary ammonium cation represented by the formula (A-1a) by condensation reaction of a quaternary ammonium salt compound to be used as a material and an anthracene compound will be described.

Typical chemical equation for the reaction is shown below,

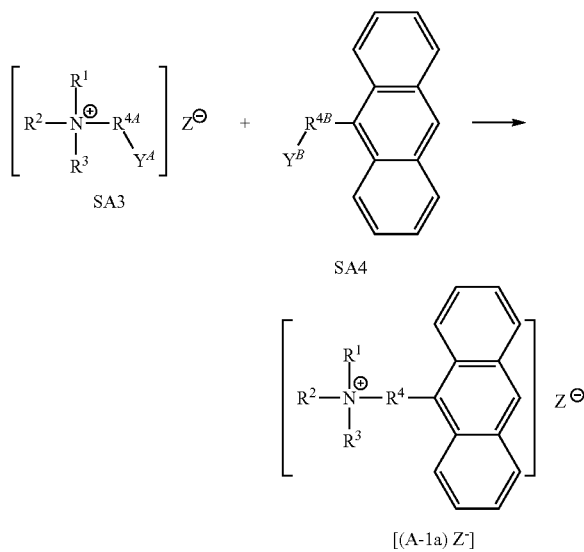

wherein $R^1$, $R^2$, $R^3$, and $R^4$ have the same meanings as above; $R^{4A}$ and $R^{4B}$ each represent a single bond or a divalent group, and $—R^{4A}—R^{4B}—$ is equal to $—R^4—$; $Y^A$ and $Y^B$ each represent a hydrogen atom, a cationic group, or a leaving group; and $Z^-$ represents a counter anion of a quaternary ammonium cation.

Illustrative examples of $R^1$, $R^2$, $R^3$, and $R^4$ include the same as exemplified above.

$R^{4A}$ and $R^{4B}$ each represent a single bond or a divalent group, and $—R^{4A}—R^{4B}—$ is equal to $—R^4—$. For example, when $R^4$ is a methylene group, $R^{4A}$ and $R^{4B}$ are a single bond and a methylene group, or a methylene group and a single bond. When $R^4$ is an ethylene group, $R^{4A}$ and $R^{4B}$ are a single bond and an ethylene group, a methylene group and a methylene group, or an ethylene group and a single bond.

$Y^A$ and $Y^B$ each independently represent a hydrogen atom, a cationic group, or a leaving group. Illustrative example thereof include hydrogen atom; cationic group such as —Li, —Na, —K, —Cu, —(Ca)$_{1/2}$, —(Mg)$_{1/2}$, —(Zn)$_{1/2}$, —MgCl, —MgBr, —MgI, —ZnCl, —ZnBr, tertiary ammonium, quaternary ammonium, quaternary phosphonium, tertiary sulfonium; and leaving group e.g. halogen atom such as chlorine atom, bromine atom; and iodine atom, alkylsulfonyloxy group such as methanesulfonyloxy group, and arylsulfonyloxy group such as p-toluenesulfonyloxy group. $—R^{4A}—R^{4B}—$ and $Y^A—Y^B$ are produced from $R^{4A}$, $R^{4B}$, $Y^A$, and $Y^B$ by condensation reaction of $—R^{4A}—Y^A$ and $Y^B—R^{4B}—$.

$Z^-$ represents a counter anion of a quaternary ammonium cation. Illustrative example thereof include OH$^-$, Cl$^-$, Br$^-$, I$^-$, (SO$_4^{2-}$)$_{1/2}$, NO$_3^-$, CH$_3$OSO$_3^-$, HSO$_4^-$, HCO$_3^-$, (CO$_3^{2-}$)$_{1/2}$, ClO$_4^-$, alkanesulfonate ion, arenesulfonate ion, and carboxylate ion.

The amount of the quaternary ammonium salt compound (SA3) to be used as a material is desirably in the range of 0.3 to 50 mol, more desirably 0.8 to 10 mol per 1 mol of the anthracene compound (SA4). The reaction is performed in a solvent or without solvent.

Examples of the solvent include alcohols such as methanol, ethanol, isopropyl alcohol, tert-butyl alcohol, and ethylene glycol; hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform, and 1,2-dichloroethylene; aprotic polar solvents such as N,N-dimethylformamide, N,N-dimethylacetamide, dimethyl sulfoxide, and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. A suitable solvent or solvents may be selected from these, and used alone or in combination with two or more kinds thereof depending on reaction conditions.

The reaction temperature may be selected in the range of −20° C. to 200° C., depending on the desired reaction rate.

Also, a base may be added to the reaction system for promoting the reaction. Examples of the base to be added include amines such as pyridine, triethylamine, diisopropylethylamine, 4-dimethylaminopyridine, and imidazole; metal alkoxides such as sodium methoxide, sodium ethoxide, and potassium tert-butoxide; carbonates such as sodium carbonate, potassium carbonate, and cesium carbonate; hydroxides such as sodium hydroxide, potassium hydroxide, and tetramethylammonium hydroxide; metal hydrides such as sodium hydride and potassium hydride; organometallic compounds such as butyl lithium and ethyl magnesium bromide; and metal amides such as lithium diisopropyl amide. A suitable base or bases may be selected from these, and used alone or in combination with two or more kinds thereof depending on reaction conditions.

The amount of the base to be used is desirably in the range of 0.3 to 10 mol, more desirably 0.5 to 5 mol per 1 mol of the anthracene compound (SA4).

Also, a catalyst may be added for accelerating the reaction rate. Examples thereof include iodides such as sodium iodide, lithium iodide, and tetrabutylammonium iodide; and bromides such as sodium bromide, lithium bromide, and tetrabutylammonium bromide.

The amount of the catalyst to be used is in the range of desirably 0.001 to 2 mol, more desirably 0.005 to 0.5 mol per 1 mol of the anthracene compound (SA4).

In view of yield, the reaction time is desirably determined by monitoring the reaction process by gas chromatography (GC) or thin-layer chromatography (TLC) so as to bring the reaction to completion. Usually the reaction time is about 0.1 to 100 hours.

After completion of the reaction, a quaternary ammonium salt compound containing an anthracene structure can be obtained by concentrating the reaction mixture. If necessary, the compound may be purified by standard techniques like water-washing, chromatography, and recrystallization.

Alternatively, a poor solvent may be added to the reaction solution, thereby the target compound is directly crystalized and purified from the reaction solvent.

[Anion Exchange]

If a counter anion X⁻ or Z⁻ of a quaternary ammonium cation containing an anthracene structure obtained by the above reaction is different from an anion species A⁻ of the inventive quaternary ammonium salt compound represented by the formula (A-1), which is a desired compound, anion exchange may be carried out as an additional process by reacting with $M^{m+}(A^-)_m$ as shown in the following chemical equation, thereby the desired compound, the quaternary ammonium salt compound of the present invention represented by the formula (A-1), can be obtained.

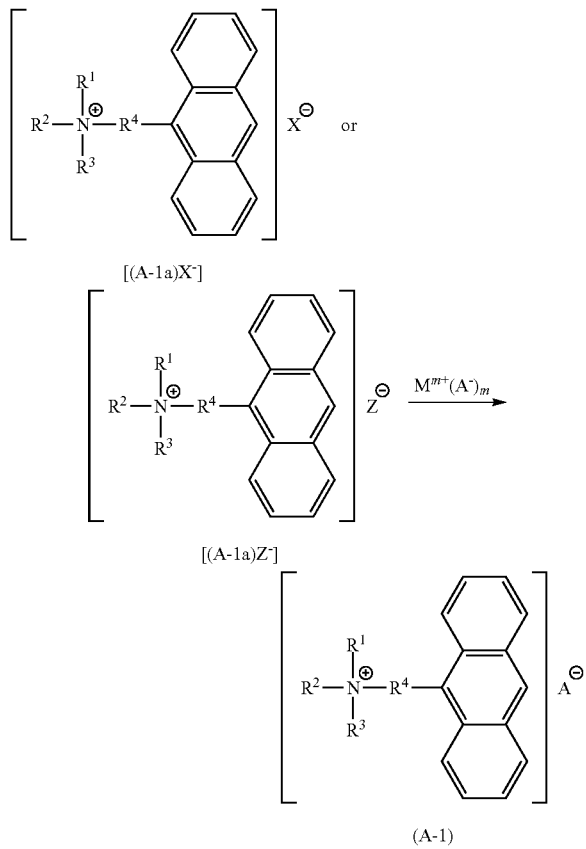

In the formula, $R^1$, $R^2$, $R^3$, $R^4$, X⁻, Z⁻, and A⁻ have the same meanings as above; $M^{m+}$ represents a m-valent organic cation or inorganic cation wherein m represents an integer of 1 to 4.

Illustrative examples of $R^1$, $R^2$, $R^3$, $R^4$, X⁻, Z⁻, and A⁻ include the same as exemplified above.

$M^{m+}$ represents a m-valent organic cation or inorganic cation. Illustrative example thereof include inorganic cation such as sodium ion, potassium ion, lithium ion, calcium ion, barium ion, silver ion, lead ion, and ammonium ion; and organic cation such as tetramethylammonium ion, triethylammonium ion, triphenyl sulfonium ion, and tetramethyl phosphonium ion.

The anion exchange reaction of a quaternary ammonium salt compound shown in the above chemical equation will be described in detail. The amount of $M^{m+}(A^-)_m$ to be used is desirably in the range of 0.5 to 10 mol, more desirably 0.8 to 5 mol per 1 mol of a starting material.

The reaction is preferably performed in a solvent. Examples of the solvent include alcohols such as methanol, ethanol, isopropyl alcohol, tert-butyl alcohol, and ethylene glycol; hydrocarbons such as hexane, heptane, benzene, toluene, and xylene; ethers such as diethyl ether, dibutyl ether, tetrahydrofuran, 1,4-dioxane, and diglyme; chlorinated solvents such as methylene chloride, chloroform, and 1,2-dichloroethylene; aprotic polar solvents such as N,N-dimethylformamide, N,N-dimethylacetamide, dimethyl sulfoxide, and N-methylpyrrolidone; carboxylic acids such as formic acid and acetic acid; esters such as ethyl acetate and butyl acetate; ketones such as acetone, 2-butanone, and 4-methyl-2-pentanone; nitriles such as acetonitrile; amines such as pyridine and triethylamine; and water. A suitable solvent or solvents may be selected from these, and used alone or in combination with two or more kinds thereof depending on reaction conditions.

The reaction temperature may be selected in the range of −20° C. to the boiling point of the solvent to be used, depending on the desired reaction rate.

In view of yield, the reaction time is desirably determined by monitoring the reaction process by liquid chromatography (LC) or thin-layer chromatography (TLC) so as to bring the reaction to completion. Usually the reaction time is about 0.1 to 100 hours.

After completion of the reaction, a target compound can be obtained by removing impurities by filtration, water-washing, or the like, and then concentrating the reaction mixture. If necessary, the compound may be purified by standard techniques like chromatography and recrystallization.

By adding such a quaternary ammonium salt compound to a composition for forming a resist under layer film, a resist under layer film which can suppress reflection particularly in KrF exposure process, and has excellent adhesiveness to a resist pattern formed thereon can be formed.

<Composition for Forming a Resist Under Layer Film>

Also, the present invention provides a composition for forming a resist under layer film which includes the quaternary ammonium salt compound of the present invention and a polysiloxane.

In the composition for forming a resist under layer film of the present invention, the quaternary ammonium salt compound of the present invention can be used alone or in combination with two or more kinds thereof.

The amount of the quaternary ammonium salt compound to be added is preferably in the range of 0.01 to 50 parts by mass, more preferably 0.1 to 40 parts by mass, based on 100 parts by mass of a base polymer (e.g. a later-described polysiloxane).

[Polysiloxane]

The polysiloxane contained in the composition for forming a resist under layer film of the present invention preferably includes one or more members selected from a compound represented by the following formula (B-1), a hydrolysate of the compound, a condensate of the compound, and a hydrolysis condensate of the compound, $$R^{1B}{}_{B1}R^{2B}{}_{B2}R^{3B}{}_{B3}Si(OR^{OB})_{(4-B1-B2-B3)} \tag{B-1}$$

wherein, $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy 0≤B1+B2+B3≤3.

A hydrolysable silicon compound (alkoxy silane) represented by the formula (B-1) used as a stating material of the polysiloxane can be exemplified by the following.

Illustrative examples of tetraalkoxy silane include tetramethoxy silane, tetraethoxy silane, tetrapropoxy silane, tetraisopropoxy silane, etc.

Illustrative examples of trialkoxy silane include trimethoxy silane, triethoxy silane, tripropoxy silane, triisopropoxy silane, methyl trimethoxy silane, methyl triethoxy silane, methyl tripropoxy silane, methyl triisopropoxy silane, ethyl trimethoxy silane, ethyl triethoxy silane, ethyl tripropoxy silane, ethyl triisopropoxy silane, vinyl trimethoxy silane, vinyl triethoxy silane, vinyl tripropoxy silane, vinyl triisopropoxy silane, propyl trimethoxy silane, propyl triethoxy silane, propyl tripropoxy silane, propyl triisopropoxy silane, isopropyl trimethoxy silane, isopropyl triethoxy silane, isopropyl tripropoxy silane, isopropyl triisopropoxy silane, butyl trimethoxy silane, butyl triethoxy silane, butyl tripropoxy silane, butyl triisopropoxy silane, sec-butyl trimethoxy silane, sec-butyl triethoxy silane, sec-butyl tripropoxy silane, sec-butyl triisopropoxy silane, tert-butyl trimethoxy silane, tert-butyl triethoxy silane, tert-butyl tripropoxy silane, tert-butyl triisopropoxy silane, cyclopropyl trimethoxy silane, cyclopropyl triethoxy silane, cyclopropyl tripropoxy silane, cyclopropyl triisopropoxy silane, cyclobutyl trimethoxy silane, cyclobutyl triethoxy silane, cyclobutyl tripropoxy silane, cyclobutyl triisopropoxy silane, cyclopentyl trimethoxy silane, cyclopentyl triethoxy silane, cyclopentyl tripropoxy silane, cyclopentyl triisopropoxy silane, cyclohexyl trimethoxy silane, cyclohexyl triethoxy silane, cyclohexyl tripropoxy silane, cyclohexyl triisopropoxy silane, cyclohexenyl trimethoxy silane, cyclohexenyl triethoxy silane, cyclohexenyl tripropoxy silane, cyclohexenyl triisopropoxy silane, cyclohexenylethyl trimethoxy silane, cyclohexenylethyl triethoxy silane, cyclohexenylethyl tripropoxy silane, cyclohexenylethyl triisopropoxy silane, cyclooctyl trimethoxy silane, cyclooctyl triethoxy silane, cyclooctyl tripropoxy silane, cyclooctyl triisopropoxy silane, cyclopentadienylpropyl trimethoxy silane, cyclopentadienylpropyl triethoxy silane, cyclopentadienylpropyl tripropoxy silane, cyclopentadienylpropyl triisopropoxy silane, bicycloheptenyl trimethoxy silane, bicycloheptenyl triethoxy silane, bicycloheptenyl tripropoxy silane, bicycloheptenyl triisopropoxy silane, bicycloheptyl trimethoxy silane, bicycloheptyl triethoxy silane, bicycloheptyl tripropoxy silane, bicycloheptyl triisopropoxy silane, adamantyl trimethoxy silane, adamantyl triethoxy silane, adamantyl tripropoxy silane, adamantyl triisopropoxy silane, phenyl trimethoxy silane, phenyl triethoxy silane, phenyl tripropoxy silane, phenyl triisopropoxy silane, benzyl trimethoxy silane, benzyl triethoxy silane, benzyl tripropoxy silane, benzyl triisopropoxy silane, tolyl trimethoxy silane, tolyl triethoxy silane, tolyl tripropoxy silane, tolyl triisopropoxy silane, anisyl trimethoxy silane, anisyl triethoxy silane, anisyl tripropoxy silane, anisyl triisopropoxy silane, phenethyl trimethoxy silane, phenethyl triethoxy silane, phenethyl tripropoxy silane, phenethyl triisopropoxy silane, naphthyl trimethoxy silane, naphthyl triethoxy silane, naphthyl tripropoxy silane, naphthyl triisopropoxy silane, etc.

Illustrative examples of dialkoxy silane include dimethyl dimethoxy silane, dimethyl diethoxy silane, methyl ethyl dimethoxy silane, methyl ethyl diethoxy silane, dimethyl dipropoxy silane, dimethyl diisopropoxy silane, diethyl dimethoxy silane, diethyl diethoxy silane, diethyl dipropoxy silane, diethyl diisopropoxy silane, dipropyl dimethoxy silane, dipropyl diethoxy silane, dipropyl dipropoxy silane, dipropyl diisopropoxy silane, diisopropyl dimethoxy silane, diisopropyl diethoxy silane, diisopropyl dipropoxy silane, diisopropyl diisopropoxy silane, dibutyl dimethoxy silane, dibutyl diethoxy silane, dibutyl dipropoxy silane, dibutyl diisopropoxy silane, di-sec-butyl dimethoxy silane, di-sec-butyl diethoxy silane, di-sec-butyl dipropoxy silane, di-sec-butyl diisopropoxy silane, di-tert-butyl dimethoxy silane, di-tert-butyl diethoxy silane, di-tert-butyl dipropoxy silane, di-tert-butyl diisopropoxy silane, dicyclopropyl dimethoxy silane, dicyclopropyl diethoxy silane, dicyclopropyl dipropoxy silane, dicyclopropyl diisopropoxy silane, dicyclobutyl dimethoxy silane, dicyclobutyl diethoxy silane, dicyclobutyl dipropoxy silane, dicyclobutyl diisopropoxy silane, dicyclopentyl dimethoxy silane, dicyclopentyl diethoxy silane, dicyclopentyl dipropoxy silane, dicyclopentyl diisopropoxy silane, dicyclohexyl dimethoxy silane, dicyclohexyl diethoxy silane, dicyclohexyl dipropoxy silane, dicyclohexyl diisopropoxy silane, dicyclohexenyl dimethoxy silane, dicyclohexenyl diethoxy silane, dicyclohexenyl dipropoxy silane, dicyclohexenyl diisopropoxy silane, dicyclohexenylethyl dimethoxy silane, dicyclohexenylethyl diethoxy silane, dicyclohexenylethyl dipropoxy silane, dicyclohexenylethyl diisopropoxy silane, dicyclooctyl dimethoxy silane, dicyclooctyl diethoxy silane, dicyclooctyl dipropoxy silane, dicyclooctyl diisopropoxy silane, dicyclopentadienylpropyl dimethoxy silane, dicyclopentadienylpropyl diethoxy silane, dicyclopentadienylpropyl dipropoxy silane, dicyclopentadienylpropyl diisopropoxy silane, bis(bicycloheptenyl)dimethoxy silane, bis(bicycloheptenyl)diethoxy silane, bis(bicycloheptenyl)dipropoxy silane, bis(bicycloheptenyl)diisopropoxy silane, bis(bicycloheptyl)dimethoxy silane, bis(bicycloheptyl)diethoxy silane, bis(bicycloheptyl)dipropoxy silane, bis(bicycloheptyl)diisopropoxy silane, diadamantyl dimethoxy silane, diadamantyl diethoxy silane, diadamantyl dipropoxy silane, diadamantyl diisopropoxy silane, diphenyl dimethoxy silane, diphenyl diethoxy silane, methyl phenyl dimethoxy silane, methyl phenyl diethoxy silane, diphenyl dipropoxy silane, diphenyl diisopropoxy silane, etc.

Illustrative examples of monoalkoxy silane include trimethyl methoxy silane, trimethyl ethoxy silane, dimethyl ethyl methoxy silane, dimethyl ethyl ethoxy silane, dimethyl phenyl methoxy silane, dimethyl phenyl ethoxy silane, dimethyl benzyl methoxy silane, dimethyl benzyl ethoxy silane, dimethyl phenethyl methoxy silane, dimethyl phenethyl ethoxy silane, etc.

Other examples of the compound represented by the formula (B-1) include those having the following structures whose silicon is bonded to one to three methoxy groups, ethoxy groups, propoxy groups, butoxy groups, pentoxy groups, cyclopentoxy groups, hexyloxy groups, and cyclohexyloxy groups as hydrolysable group, $OR^{OB}$.

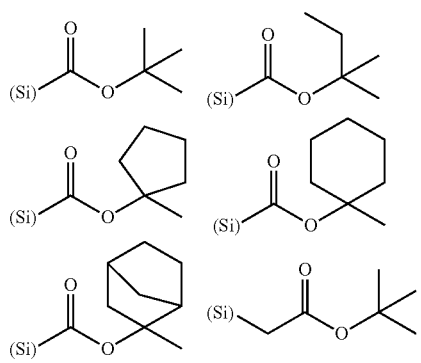

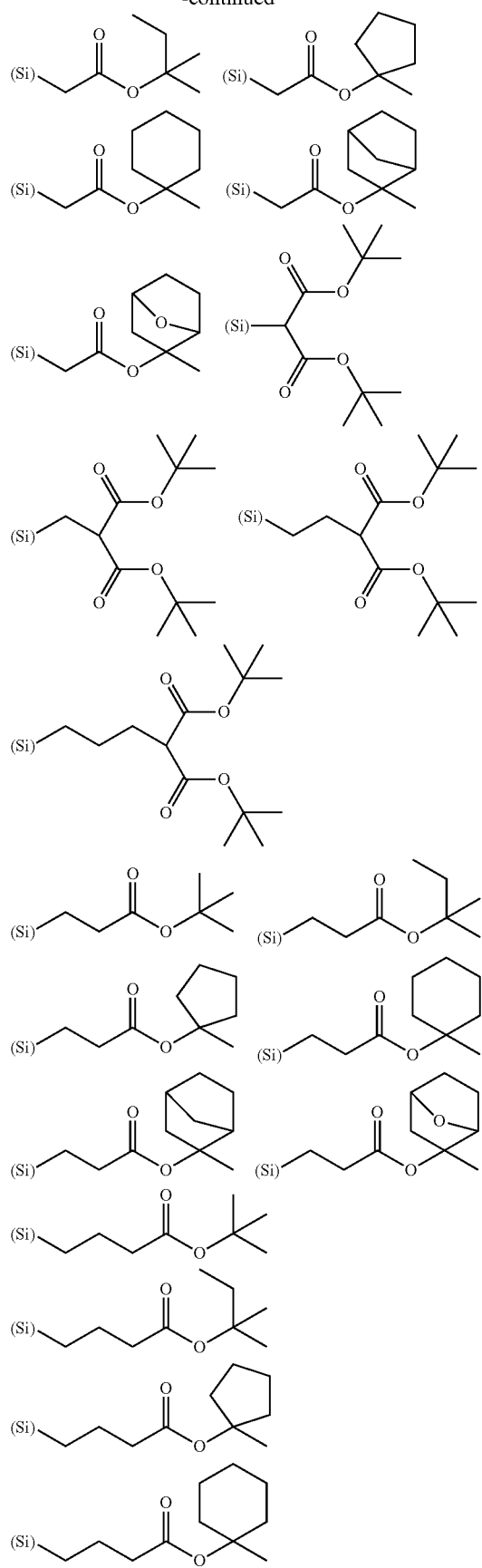
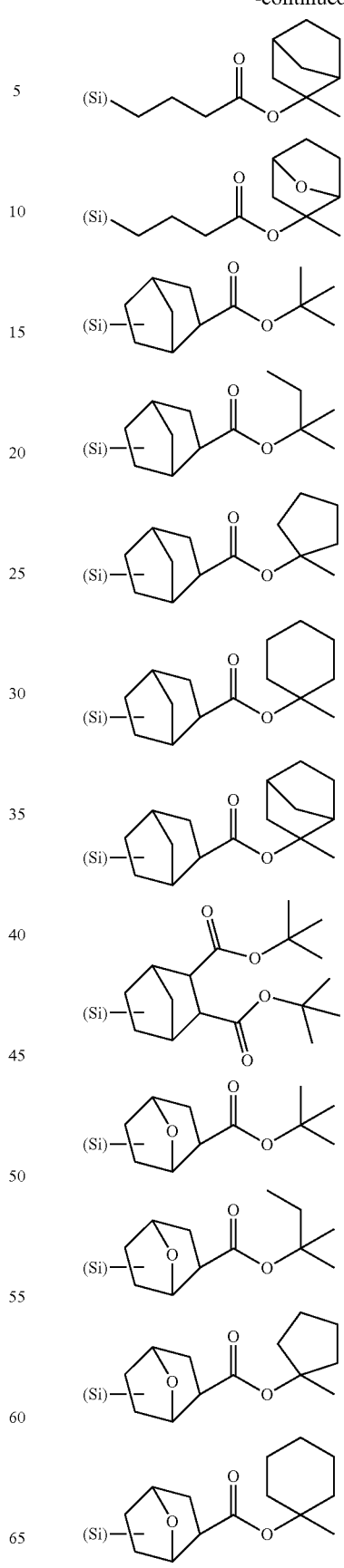

-continued
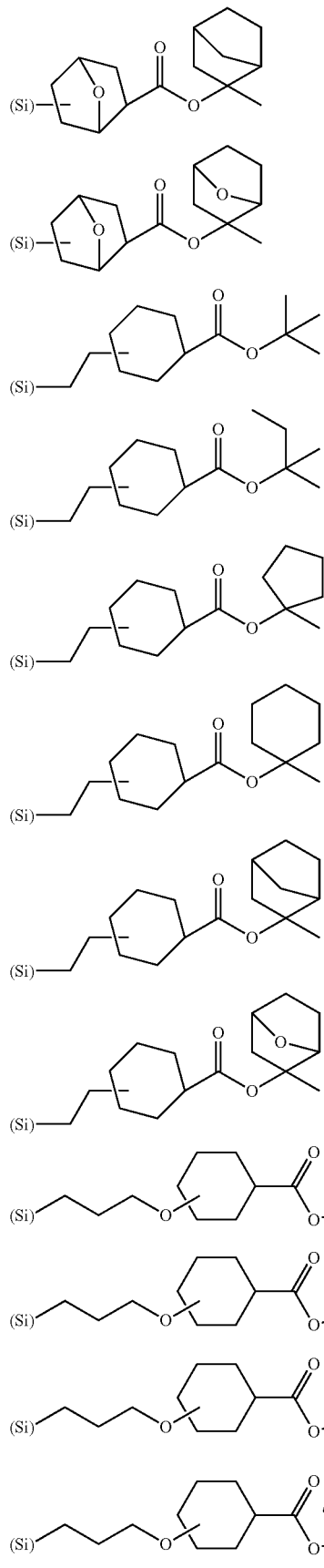
-continued
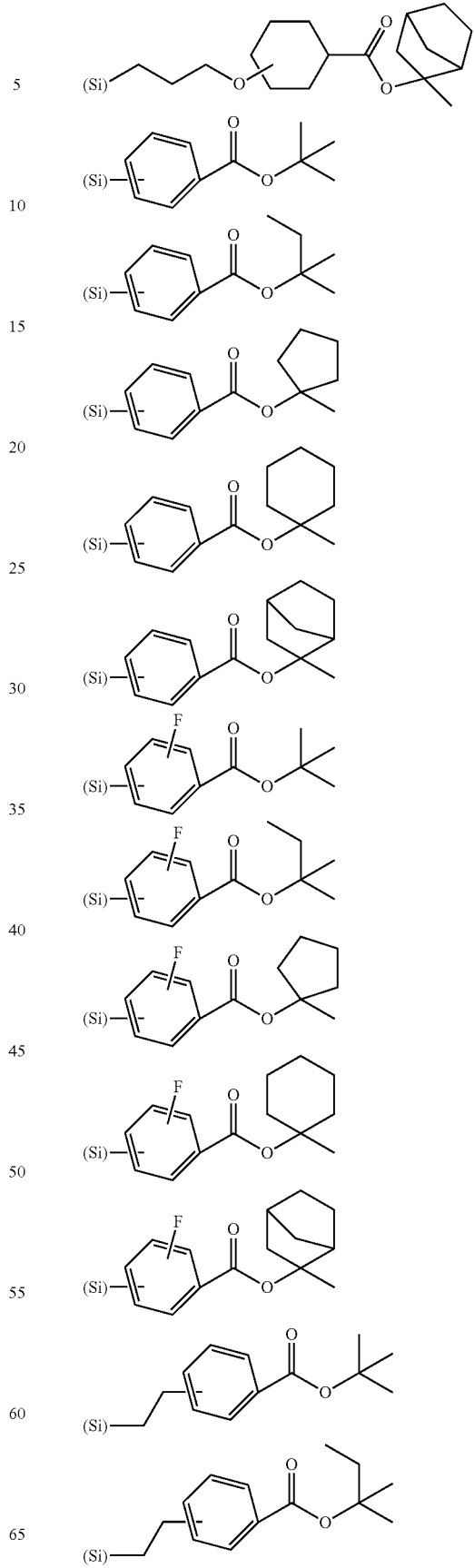

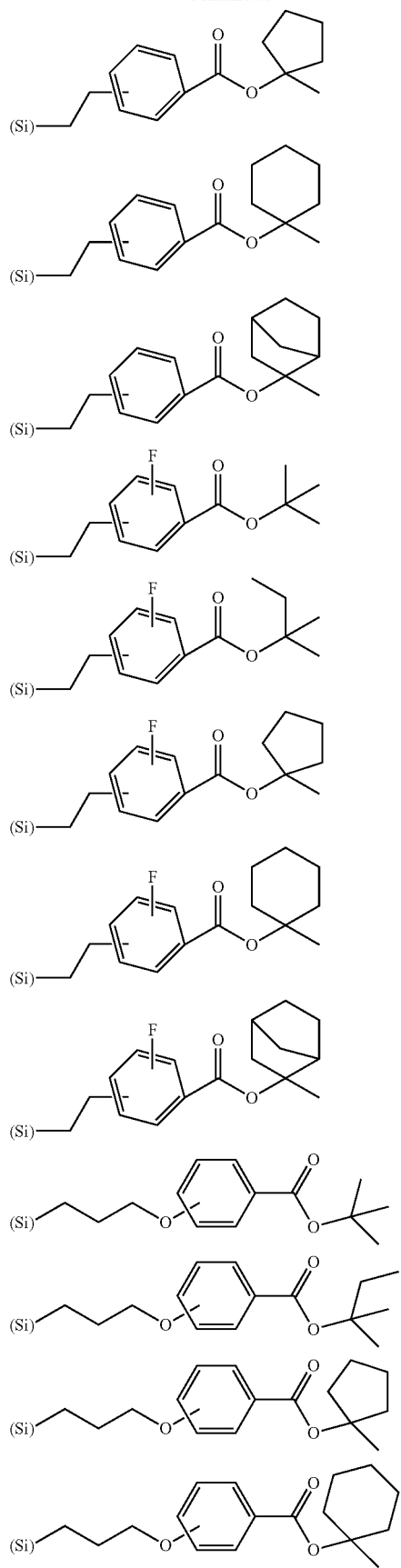
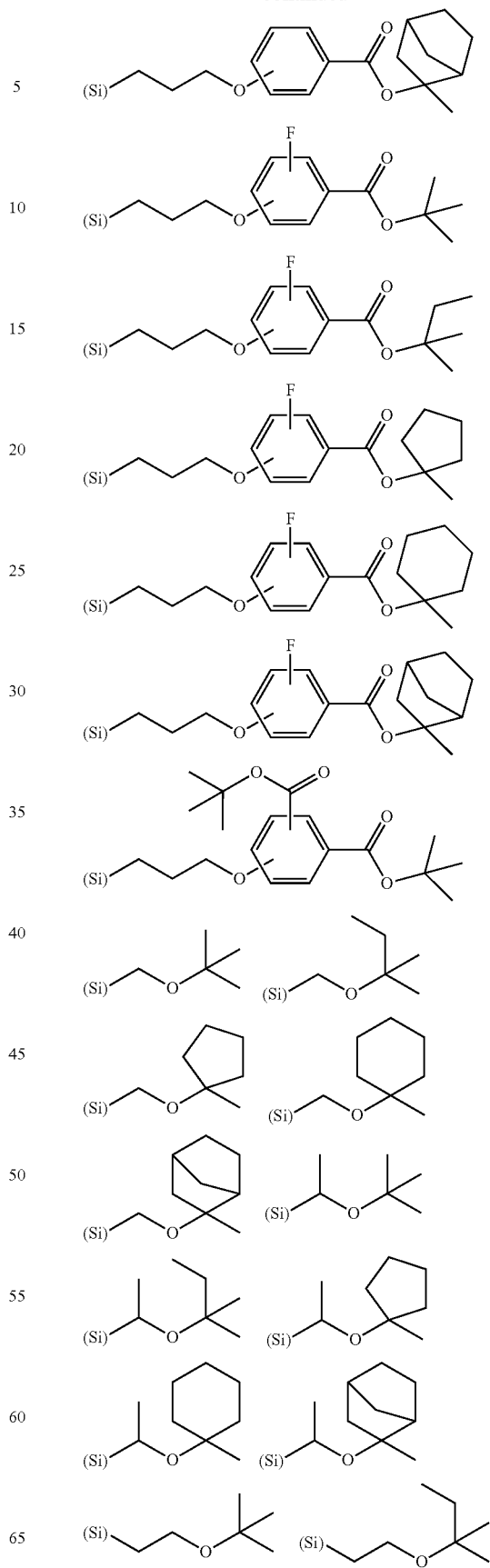

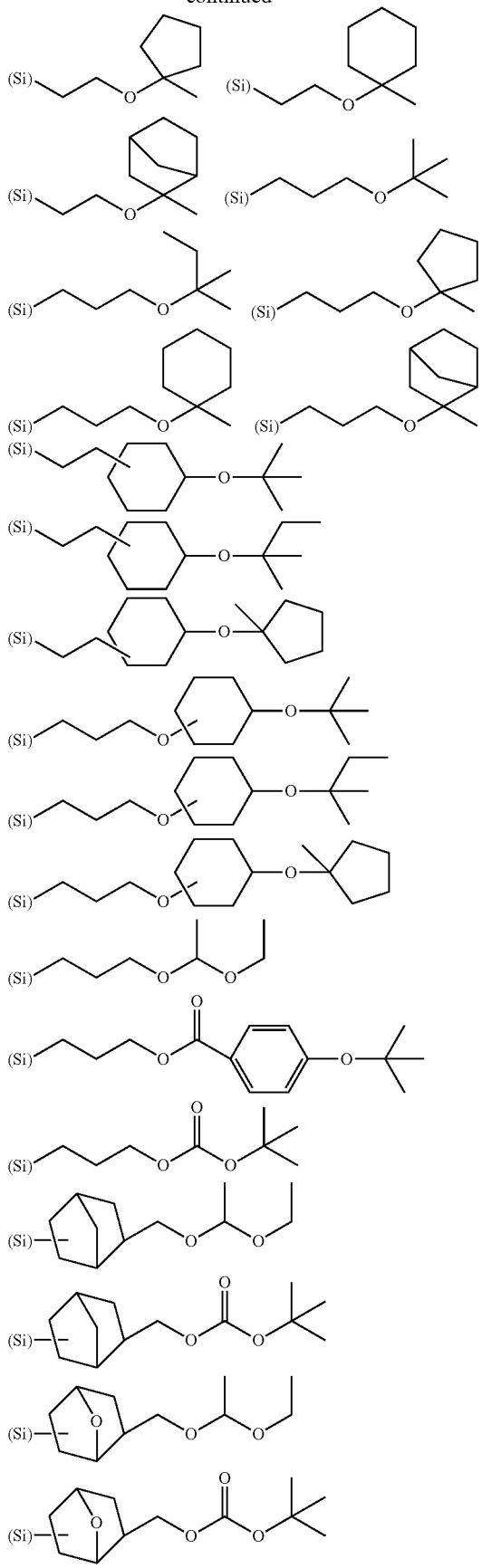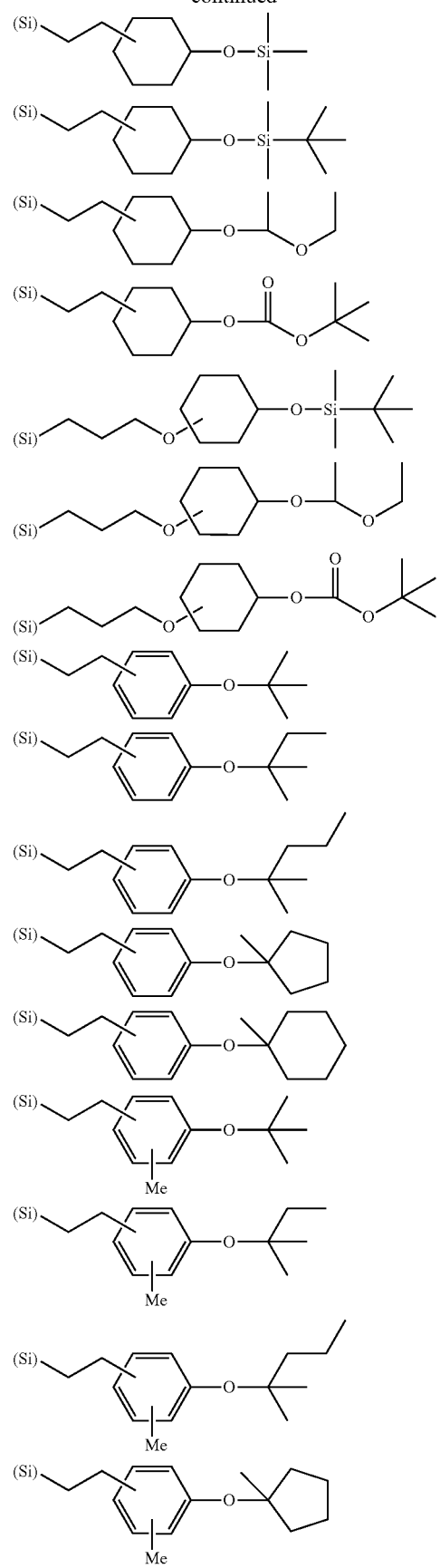

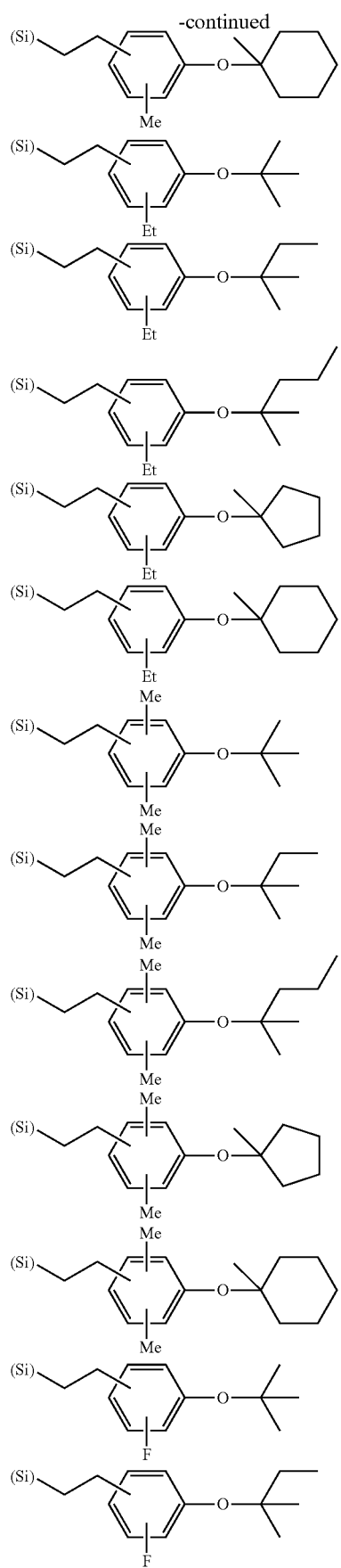
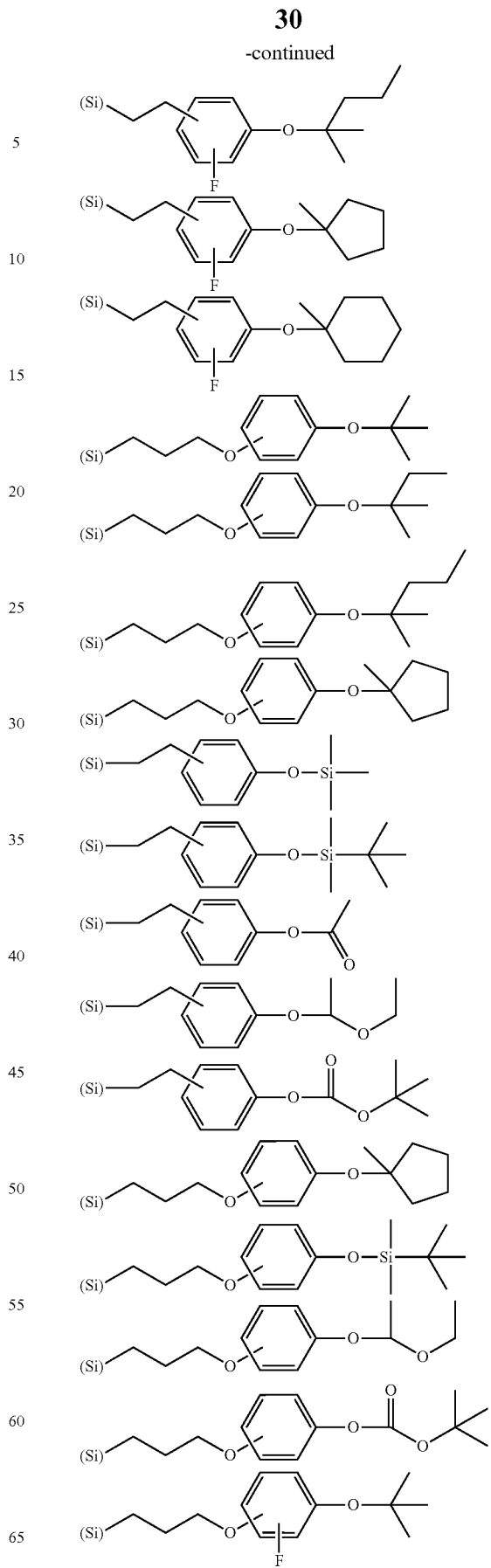

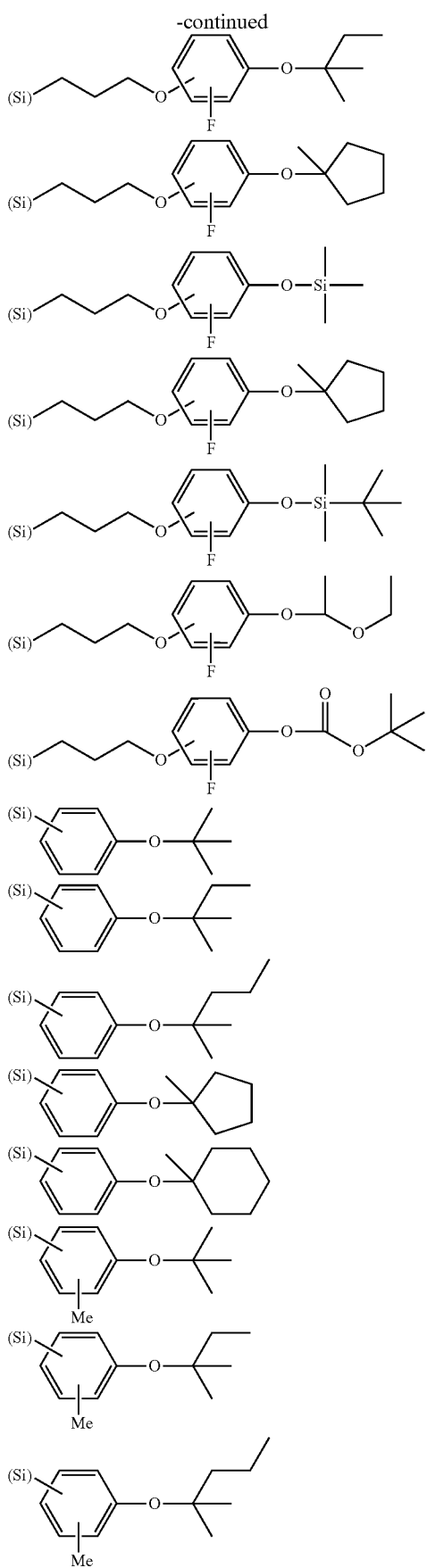

-continued
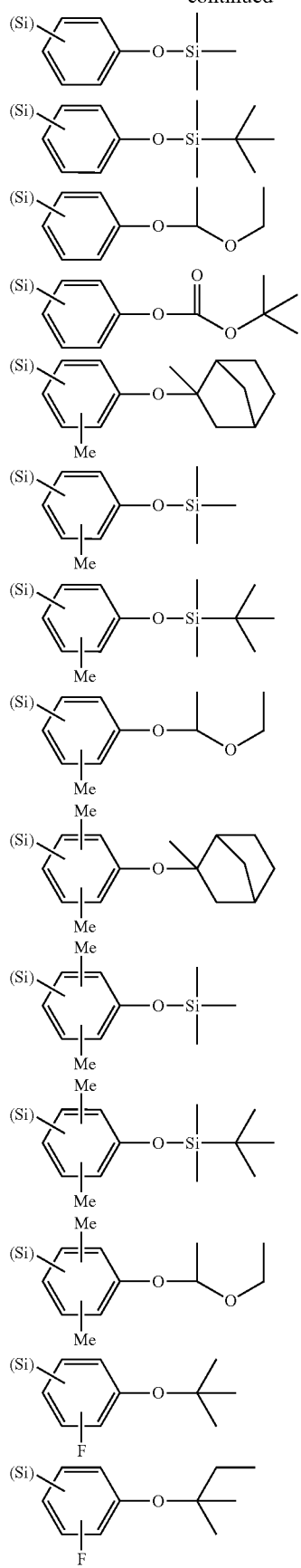
-continued
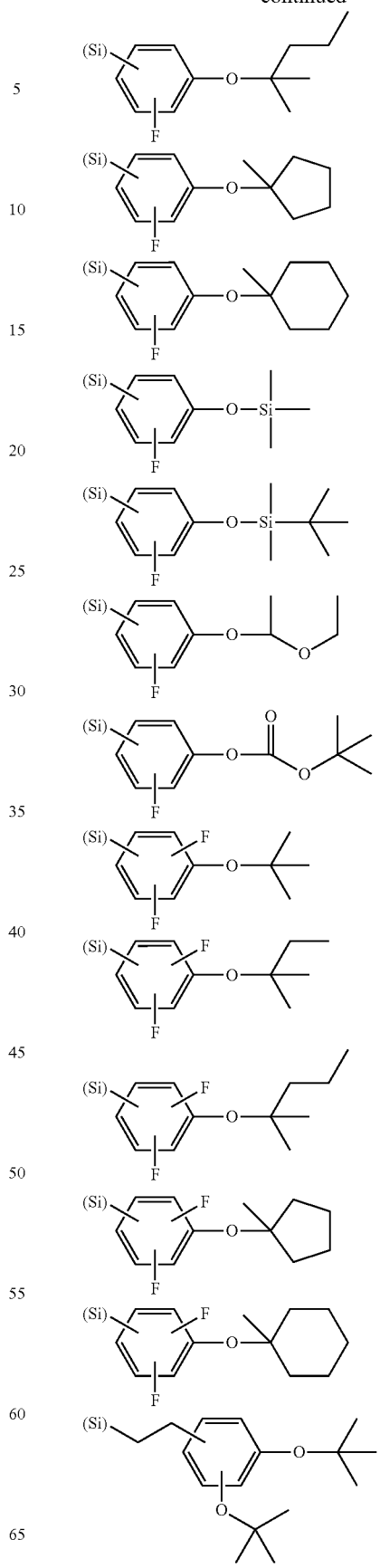

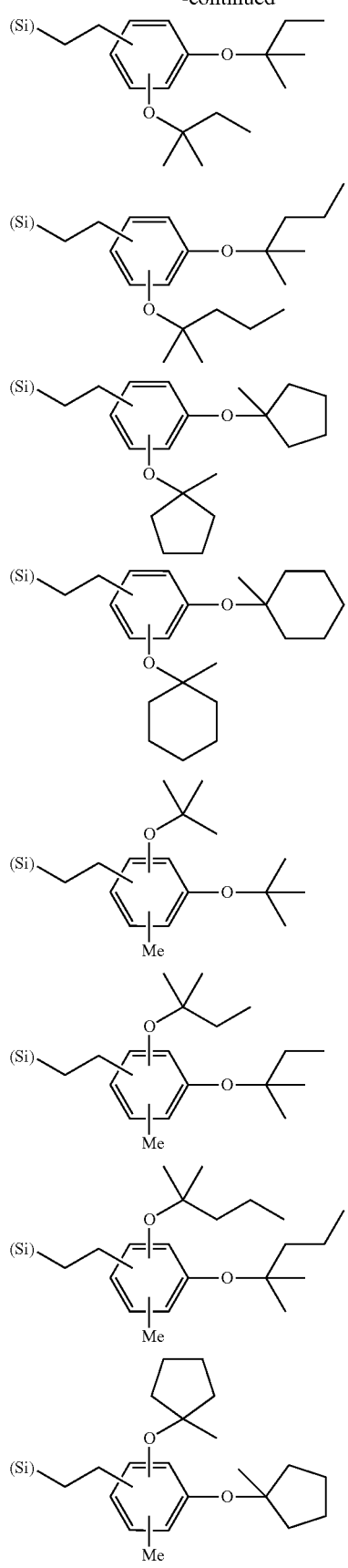
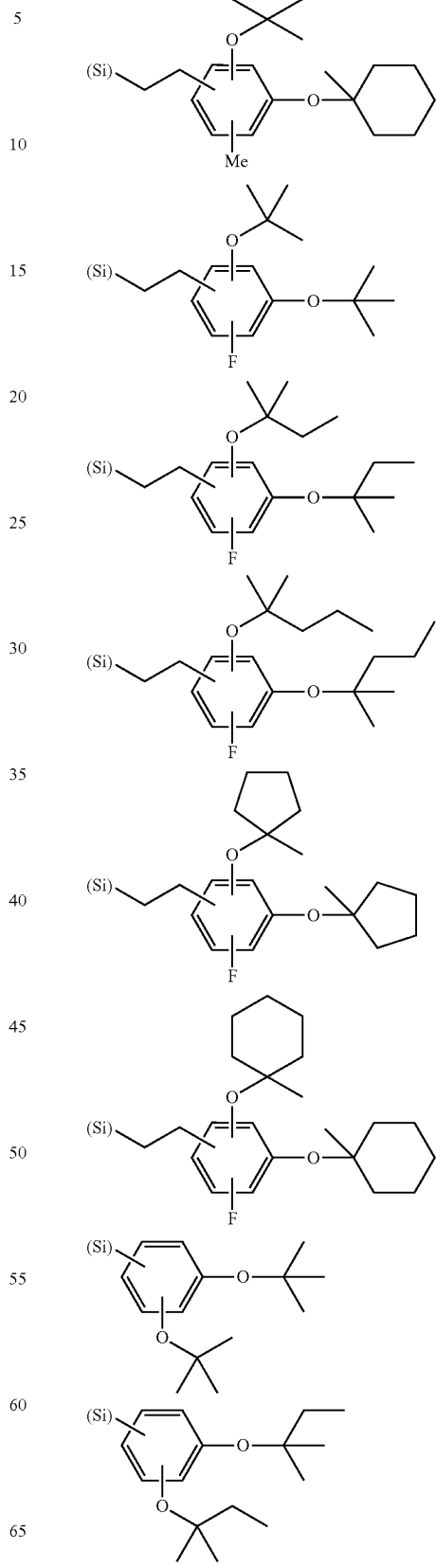

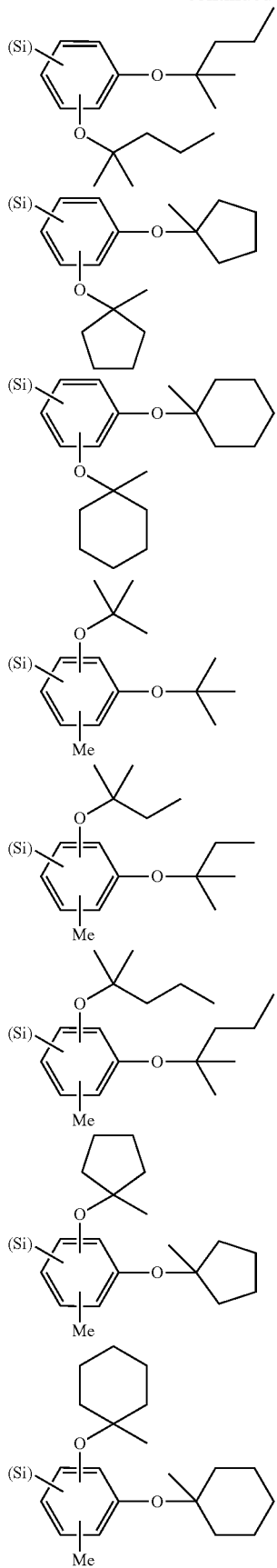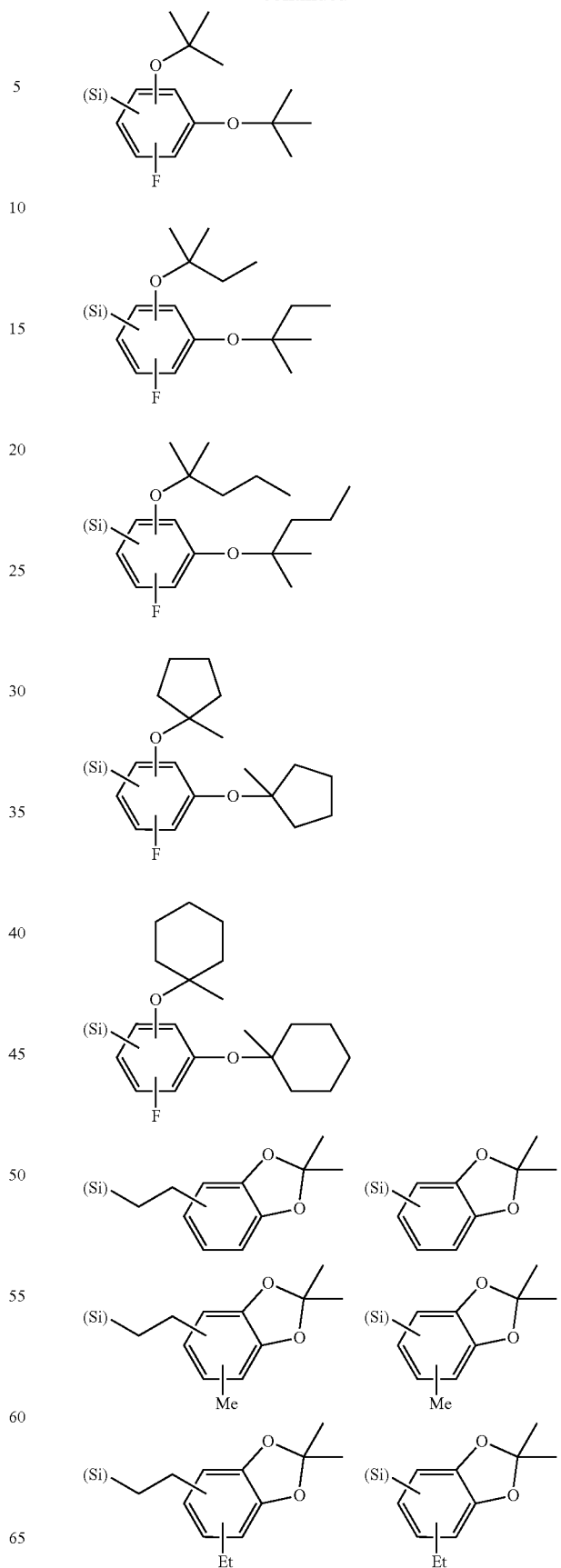

-continued

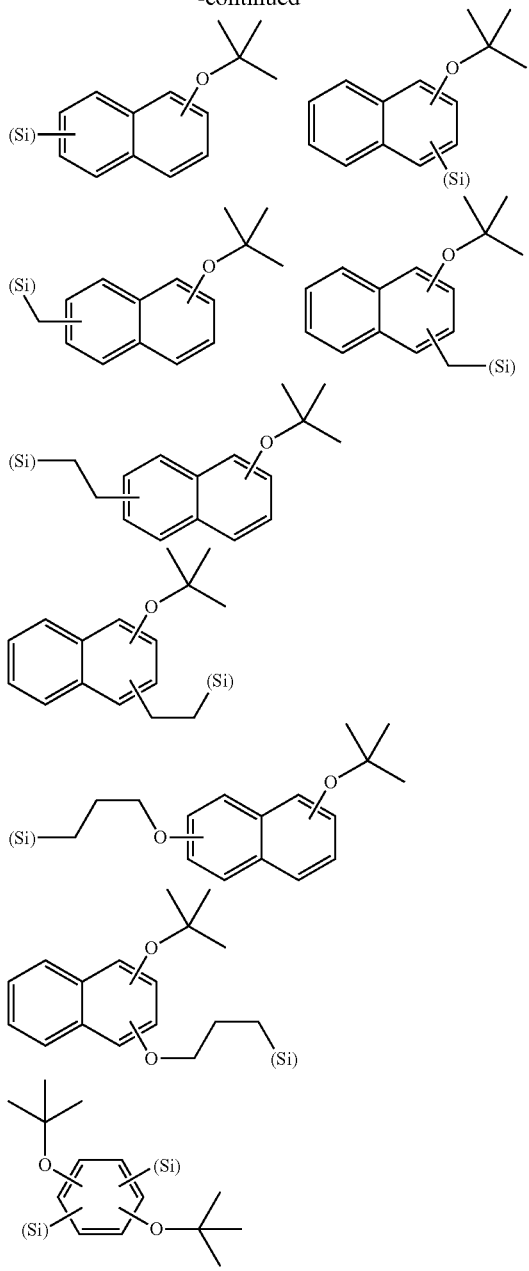

The polysiloxane contained in the composition for forming a resist under layer film of the present invention may contain a hydrolysable metal compound represented by the following formula (B-2) as a starting material, in addition to the compound represented by the formula (B-1), $$L'(OR^{4B})_{B4}(OR^{5B})_{B5}(O)_{B6} \quad (B-2)$$

wherein $R^{4B}$ and $R^{5B}$ represent a hydrogen atom or an organic group having 1 to 30 carbon atoms; B4, B5, and B6 represent an integer of 0 or more, and B4+B5+B6 is a number of valency determined by L'; and L' represents an element belonging to the group III, IV, or V in the periodic table except for a carbon.

Illustrative examples of the hydrolysable metal compound represented by the formula (B-2) include the following compounds.

In the case that L' is boron, illustrative examples of the compound represented by the formula (B-2) include boron methoxide, boron ethoxide, boron propoxide, boron butoxide, boron amyloxide, boron hexyloxide, boron cyclopentoxide, boron cyclohexyloxide, boron allyloxide, boron phenoxide, boron methoxyethoxide, boric acid, and boron oxide.

In the case that L' is aluminum, illustrative examples of the compound represented by the formula (B-2) include aluminum methoxide, aluminum ethoxide, aluminum propoxide, aluminum butoxide, aluminum amyloxide, aluminum hexyloxide, aluminum cyclopentoxide, aluminum cyclohexyloxide, aluminum allyloxide, aluminum phenoxide, aluminum methoxyethoxide, aluminum ethoxyethoxide, aluminum dipropoxyethyl acetoacetate, aluminum dibutoxyethyl acetoacetate, aluminum propoxy bisethyl acetoacetate, aluminum butoxy bisethyl acetoacetate, aluminum 2,4-pentanedionate, and aluminum 2,2,6,6-tetramethyl-3,5-heptanedionate.

In the case that L' is gallium, illustrative examples of the compound represented by the formula (B-2) include gallium methoxide, gallium ethoxide, gallium propoxide, gallium butoxide, gallium amyloxide, gallium hexyloxide, gallium cyclopentoxide, gallium cyclohexyloxide, gallium allyloxide, gallium phenoxide, gallium methoxyethoxide, gallium ethoxyethoxide, gallium dipropoxyethyl acetoacetate, gallium dibutoxyethyl acetoacetate, gallium propoxy bisethyl acetoacetate, gallium butoxy bisethyl acetoacetate, gallium 2,4-pentanedionate, and gallium 2,2,6,6-tetramethyl-3,5-heptanedionate.

In the case that L' is yttrium, illustrative examples of the compound represented by the formula (B-2) include yttrium methoxide, yttrium ethoxide, yttrium propoxide, yttrium butoxide, yttrium amyloxide, yttrium hexyloxide, yttrium cyclopentoxide, yttrium cyclohexyloxide, yttrium allyloxide, yttrium phenoxide, yttrium methoxyethoxide, yttrium ethoxyethoxide, yttrium dipropoxyethyl acetoacetate, yttrium dibutoxyethyl acetoacetate, yttrium propoxy bisethyl acetoacetate, yttrium butoxy bisethyl acetoacetate, yttrium 2,4-pentanedionate, and yttrium 2,2,6,6-tetramethyl-3,5-heptanedionate.

In the case that L' is germanium, illustrative examples of the compound represented by the formula (B-2) include germanium methoxide, germanium ethoxide, germanium propoxide, germanium butoxide, germanium amyloxide, germanium hexyloxide, germanium cyclopentoxide, germanium cyclohexyloxide, germanium allyloxide, germanium phenoxide, germanium methoxyethoxide, and germanium ethoxyethoxide.

In the case that L' is titanium, illustrative examples of the compound represented by the formula (B-2) include titanium methoxide, titanium ethoxide, titanium propoxide, titanium butoxide, titanium amyloxide, titanium hexyloxide, titanium cyclopentoxide, titanium cyclohexyloxide, titanium allyloxide, titanium phenoxide, titanium methoxyethoxide, titanium ethoxyethoxide, titanium dipropoxy bisethyl acetoacetate, titanium dibutoxy bisethyl acetoacetate, titanium dipropoxy bis-2,4-pentanedionate, and titanium dibutoxy bis-2,4-pentanedionate.

In the case that L' is hafnium, illustrative examples of the compound represented by the formula (B-2) include hafnium methoxide, hafnium ethoxide, hafnium propoxide, hafnium butoxide, hafnium amyloxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxy bisethyl acetoacetate, hafnium dibutoxy bisethyl acetoacetate, hafnium dipropoxy bis-2,4-pentanedionate, and hafnium dibutoxy bis-2,4-pentanedionate.

In the case that L' is tin, illustrative examples of the compound represented by the formula (B-2) include methoxy tin, ethoxy tin, propoxy tin, butoxy tin, phenoxy tin, methoxyethoxy tin, ethoxyethoxy tin, tin 2,4-pentanedionate, and tin 2,2,6,6-tetramethyl-3,5-heptanedionate.

In the case that L' is arsenic, illustrative examples of the compound represented by the formula (B-2) include methoxy arsenic, ethoxy arsenic, propoxy arsenic, butoxy arsenic, and phenoxy arsenic.

In the case that L' is antimony, illustrative examples of the compound represented by the formula (B-2) include methoxy antimony, ethoxy antimony, propoxy antimony, butoxy antimony, phenoxy antimony, antimony acetate, and antimony propionate.

In the case that L' is niobium, illustrative examples of the compound represented by the formula (B-2) include methoxy niobium, ethoxy niobium, propoxy niobium, butoxy niobium, and phenoxy niobium.

In the case that L' is tantalum, illustrative examples of the compound represented by the formula (B-2) include methoxy tantalum, ethoxy tantalum, propoxy tantalum, butoxy tantalum, and phenoxy tantalum.

In the case that L' is bismuth, illustrative examples of the compound represented by the formula (B-2) include methoxy bismuth, ethoxy bismuth, propoxy bismuth, butoxy bismuth, and phenoxy bismuth.

In the case that L' is phosphorous, illustrative examples of the compound represented by the formula (B-2) include trimethyl phosphite, triethyl phosphite, tripropyl phosphite, trimethyl phosphate, triethyl phosphate, tripropyl phosphate, and diphosphorous pentaoxide.

In the case that L' is vanadium, illustrative examples of the compound represented by the formula (B-2) include vanadium oxide bis(2,4-pentanedionate), vanadium 2,4-pentanedionate, vanadium tributoxide oxide, and vanadium tripropoxide oxide.

In the case that L' is zirconium, illustrative examples of the compound represented by the formula (B-2) include methoxy zirconium, ethoxy zirconium, propoxy zirconium, butoxy zirconium, phenoxy zirconium, zirconium dibutoxide bis(2,4-pentanedionate), and zirconium dipropoxide bis (2,2,6,6-tetramethyl-3,5-heptanedionate).

One or more compounds mentioned above may be selected and mixed before or during the reaction to be used as the starting material (monomer) for producing the polysiloxane.

The polysiloxane used in the composition for forming a resist under layer film of the present invention may be produced by hydrolysis condensation of the compounds represented by the formula (B-1), and if necessary, the compounds represented by the formula (B-2), by using one or more compounds selected from inorganic acid, aliphatic sulfonic acid, and aromatic sulfonic acid as an acid catalyst.

Illustrative examples of the acid catalyst used for the reaction include hydrofluoric acid, hydrochloric acid, hydrobromic acid, sulfuric acid, nitric acid, perchloric acid, phosphoric acid, methanesulfonic acid, benzenesulfonic acid, and toluenesulfonic acid. The amount of the catalyst to be used is usually in the range of $1\times10^{-6}$ to 10 mol, preferably $1\times10^{-5}$ to 5 mol, more preferably $1\times10^{-4}$ to 1 mol per 1 mol of the monomers.

The amount of water for obtaining the polysiloxane by hydrolysis condensation of these monomers is preferably in the range of 0.01 to 100 mol, more preferably 0.05 to 50 mol, much more preferably 0.1 to 30 mol per 1 mol of a hydrolysable substituent bonded to the monomers. If the amount is 100 mol or less, a reaction device does not become excessively large, therefore it is economical.

As an operation manner, the monomers are added to a catalyst aqueous solution to start hydrolysis condensation reaction. In the manner, an organic solvent may be added to the catalyst aqueous solution, the monomers may be diluted with an organic solvent, or both may be performed. The reaction temperature is preferably in the range of 0 to 100° C., and more preferably 5 to 80° C. A method for maintaining the temperature at 5 to 80° C. while the monomers are dropped, and then aging the mixture at 20 to 80° C. is preferable.

Illustrative examples of the organic solvent that can be added to the catalyst aqueous solution, or can dilute the monomers, include methanol, ethanol, 1-propanol, 2-propanol, 1-butanol, 2-butanol, 2-methyl-1-propanol, ethylene glycol, propylene glycol, acetone, acetonitrile, tetrahydrofuran, toluene, hexane, ethyl acetate, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxy propionate, ethyl 3-ethoxy propionate, tert-butyl acetate, tert-butyl propionate, propylene glycol mono-tert-butyl ether acetate, γ-butyrolactone, and mixture thereof.

Among them, water-soluble solvents are preferable, and illustrative examples thereof include alcohols such as methanol, ethanol, 1-propanol, and 2-propanol; polyvalent alcohols such as ethylene glycol and propylene glycol; polyvalent alcohol condensate derivatives such as butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, and ethylene glycol monopropyl ether; acetone; acetonitrile; tetrahydrofuran, etc. Particularly preferable is a solvent with a boiling point of 100° C. or less.

The amount of the organic solvent to be used is preferably in the range of 0 to 1,000 mL, and particularly preferably 0 to 500 mL per 1 mol of the monomers. If the amount is in such a range, a reaction vessel does not become excessively large, therefore it is economical.

Thereafter, if necessary, neutralization reaction of the catalyst is carried out, and alcohol produced by hydrolysis condensation reaction is removed under reduced pressure to obtain a reaction mixture aqueous solution. The amount of an alkaline substance to be used for neutralization is preferably 0.1 to 2 equivalent weight with respect to an acid used as the catalyst. The alkaline substance may be any substance so long as it shows basicity in water.

Subsequently, it is preferable that by-products such as alcohol produced by hydrolysis condensation reaction be removed from the reaction mixture. The temperature for heating the reaction mixture is preferably in the range of 0 to 100° C., more preferably 10 to 90° C., and much more preferably 15 to 80° C. though it is depending on the kinds of the added organic solvent and the alcohol produced by reaction. Degree of vacuum in this operation is preferably an atmospheric pressure or less, more preferably 80 kPa or less in the absolute pressure, and much more preferably 50 kPa or less in the absolute pressure though it is depending on the kinds of the organic solvent and the alcohol to be removed, an exhausting equipment, a condensation equipment, and heating temperature. Although it is difficult to know exactly the amount of the alcohol removed, it is preferable that about 80% by mass or more of the produced alcohol and so forth be removed.

Next, the acid catalyst used for hydrolysis condensation may be removed from the reaction mixture. A method for removing the acid catalyst may be to mix water and the polysiloxane, and then extract the polysiloxane by an organic solvent. As the organic solvent, an organic solvent that can dissolve the polysiloxane, and be separated into two layers when mixed with water is preferably used. Illustrative examples thereof include methanol, ethanol, 1-propanol, 2-propanol, 1-butanol, 2-butanol, 2-methyl-1-propanol, acetone, tetrahydrofuran, toluene, hexane, ethyl acetate, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxy propionate, ethyl 3-ethoxy propionate, tert-butyl acetate, tert-butyl propionate, propylene glycol mono-tert-butyl ether acetate, γ-butyrolactone, methyl isobutyl ketone, cyclopentyl methyl ether, etc., and mixture thereof.

Moreover, a mixture of a water-soluble organic solvent and a slightly water-soluble organic solvent can also be used. Preferable examples thereof include methanol+ethyl acetate mixture, ethanol+ethyl acetate mixture, 1-propanol+ethyl acetate mixture, 2-propanol+ethyl acetate mixture, butanediol monomethyl ether+ethyl acetate mixture, propylene glycol monomethyl ether+ethyl acetate mixture, ethylene glycol monomethyl ether+ethyl acetate mixture, butanediol monoethyl ether+ethyl acetate mixture, propylene glycol monoethyl ether+ethyl acetate mixture, ethylene glycol monoethyl ether+ethyl acetate mixture, butanediol monopropyl ether+ethyl acetate mixture, propylene glycol monopropyl ether+ethyl acetate mixture, ethylene glycol monopropyl ether+ethyl acetate mixture, methanol+methyl isobutyl ketone mixture, ethanol+methyl isobutyl ketone mixture, 1-propanol+methyl isobutyl ketone mixture, 2-propanol+methyl isobutyl ketone mixture, propylene glycol monomethyl ether+methyl isobutyl ketone mixture, ethylene glycol monomethyl ether+methyl isobutyl ketone mixture, propylene glycol monoethyl ether+methyl isobutyl ketone mixture, ethylene glycol monoethyl ether+methyl isobutyl ketone mixture, propylene glycol monopropyl ether+methyl isobutyl ketone mixture, ethylene glycol monopropyl ether+methyl isobutyl ketone mixture, methanol+cyclopentyl methyl ether mixture, ethanol+cyclopentyl methyl ether mixture, 1-propanol+cyclopentyl methyl ether mixture, 2-propanol+cyclopentyl methyl ether mixture, propylene glycol monomethyl ether+cyclopentyl methyl ether mixture, ethylene glycol monomethyl ether+cyclopentyl methyl ether mixture, propylene glycol monoethyl ether+cyclopentyl methyl ether mixture, ethylene glycol monoethyl ether+cyclopentyl methyl ether mixture, propylene glycol monopropyl ether+cyclopentyl methyl ether mixture, ethylene glycol monopropyl ether+cyclopentyl methyl ether mixture, methanol+propylene glycol methyl ether acetate mixture, ethanol+propylene glycol methyl ether acetate mixture, 1-propanol+propylene glycol methyl ether acetate mixture, 2-propanol+propylene glycol methyl ether acetate mixture, propylene glycol monomethyl ether+propylene glycol methyl ether acetate mixture, ethylene glycol monomethyl ether+propylene glycol methyl ether acetate mixture, propylene glycol monoethyl ether+propylene glycol methyl ether acetate mixture, ethylene glycol monoethyl ether+propylene glycol methyl ether acetate mixture, propylene glycol monopropyl ether+propylene glycol methyl ether acetate mixture, ethylene glycol monopropyl ether+propylene glycol methyl ether acetate mixture, etc., but are not restricted to the combination of these mixtures.

The mixing ratio of the water-soluble organic solvent and the slightly water-soluble organic solvent is appropriately determined. The amount of the water-soluble organic solvent is preferably in the range of 0.1 to 1,000 parts by mass, more preferably 1 to 500 parts by mass, and much more preferably 2 to 100 parts by mass, based on 100 parts by mass of the slightly water-soluble organic solvent.

Subsequently, the reaction mixture may be washed with neutral water. The neutral water may be water called deionized water or ultrapure water. The amount of the water is preferably in the range of 0.01 to 100 L, more preferably 0.05 to 50 L, and much more preferably 0.1 to 5 L per 1 L of the polysiloxane solution. The washing may be carried out in such a way that the both the polysiloxane solution and water are mixed in a vessel by stirring, and then settled to separate a water layer. The number of washing may be one or more, and preferably about 1 to 5 times because washing of 10 times or more is not worth to have full effects thereof.

Other methods for removing the acid catalyst include a method using an ion-exchange resin, and a method for removing an acid catalyst after neutralization with epoxy compounds such as ethylene oxide and propylene oxide. These methods can be appropriately selected according to the acid catalyst used in the reaction.

In the operation of water-washing, there is a case that a part of the polysiloxane escapes into a water layer, thereby substantially the same effect as fractionation operation is obtained. Therefore, the number of washing and the amount of water for washing may be appropriately determined in view of effects of catalyst removal and fractionation.

A final solvent is then added to the polysiloxane solution even when the acid catalyst remains therein or has been removed therefrom, and solvent-exchange is thereby performed under reduced pressure to obtain a desired solution of the polysiloxane. The temperature during the solvent exchange is preferably in the range of 0 to 100° C., more preferably 10 to 90° C., and much more preferably 15 to 80° C. though it is depending on the kinds of the reaction solvent and the extraction solvent to be removed. Degree of vacuum in this operation is preferably an atmospheric pressure or less, more preferably 80 kPa or less in the absolute pressure, and much more preferably 50 kPa or less in the absolute pressure though it is depending on the kinds of the solvents to be removed, an exhausting equipment, condensation equipment, and heating temperature.

In this operation, sometimes the polysiloxane may become unstable because the solvent was exchanged. This occurs due to compatibility of the polysiloxane with the final solvent. Thus, in order to prevent this from occurring, a monovalent, divalent, or more polyvalent alcohol having cyclic ether as a substituent may be added thereto as a stabilizer. The amount thereof to be added is preferably in the range of 0 to 25 parts by mass, more preferably 0 to 15 parts by mass, and much more preferably 0 to 5 parts by mass, or 0.5 parts by mass or more when it is added, based on 100 parts by mass of the polysiloxane contained in the solution before the solvent exchange. If necessary, a stabilizer may be added to the solution before the solvent exchange operation.

The concentration of the polysiloxane solution is preferably in the range of 0.1 to 20% by mass. If the concentration is in such a range, condensation reaction of the polysiloxane does not progress; thereby the polysiloxane does not change to the state that it cannot be dissolved into an organic solvent again. Further, if the concentration is in such a range, the amount of the solvent becomes appropriate, therefore it is economical.

Preferable examples of the final solvent added to the polysiloxane solution include alcohol solvents, and particularly monoalkyl ether derivatives of ethylene glycol, diethylene glycol, triethylene glycol, propylene glycol, dipropylene glycol, butanediol, or the like. Illustrative examples thereof include butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, etc.

In addition, if these solvents are a main solvent, a non-alcoholic solvent may be added thereinto as an adjuvant solvent. Illustrative examples of this adjuvant solvent include acetone, tetrahydrofuran, toluene, hexane, ethyl acetate, cyclohexanone, methyl amyl ketone, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxy propionate, ethyl 3-ethoxy propionate, tert-butyl acetate, tert-butyl propionate, propylene glycol mono-tert-butyl ether acetate, γ-butyrolactone, methyl isobutyl ketone, cyclopentyl methyl ether, etc.

As an alternative operation manner, water or a water-containing organic solvent may be added to the monomers or an organic solution of the monomers to start hydrolysis reaction. In the manner, the catalyst may be added to the monomers or the organic solution of the monomers, or may be added to the water or the water-containing organic solvent. The reaction temperature is preferably in the range of 0 to 100° C., and more preferably 10 to 80° C. A method for heating the mixture at 10 to 50° C. while water is dropped, and then increasing the temperature to 20 to 80° C. to age the mixture is preferable.

As the organic solvent, water-soluble solvent is preferable, and illustrative examples thereof include alcohols such as methanol, ethanol, 1-propanol, 2-propanol, 1-butanol, 2-butanol, and 2-methyl-1-propanol; polyvalent alcohol condensate derivatives such as butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, and propylene glycol monopropyl ether; acetone; tetrahydrofuran; acetonitrile, etc., and a mixture thereof.

The amount of the organic solvent to be used may be the same amount as above. A reaction mixture obtained may be post-treated like the above-mentioned method to obtain the polysiloxane.

Alternatively, the polysiloxane used in the composition for forming a resist under layer film of the present invention may be produced by hydrolysis condensation of the compounds represented by the formula (B-1), and if necessary, the compounds represented by the formula (B-2), in the presence of a base catalyst.

Illustrative examples of the base catalyst include methylamine, ethylamine, propylamine, butylamine, ethylenediamine, hexamethylenediamine, dimethylamine, diethylamine, ethylmethylamine, trimethylamine, triethylamine, tripropylamine, tributylamine, cyclohexylamine, dicyclohexylamine, monoethanolamine, diethanolamine, dimethyl-monoethanolamine, monomethyl-diethanolamine, triethanolamine, diazabicyclooctane, diazabicyclo cyclononene, diazabicycloundecene, hexamethylenetetramine, aniline, N,N-dimethylaniline, pyridine, N,N-dimethylaminopyridine, pyrrole, piperazine, pyrrolidine, piperidine, picoline, tetramethylammonium hydroxide, choline hydroxide, tetrapropylammonium hydroxide, tetrabutylammonium hydroxide, ammonia, lithium hydroxide, sodium hydroxide, potassium hydroxide, barium hydroxide, calcium hydroxide, etc. The amount of the catalyst to be used is usually in the range of $1\times10^{-6}$ to 10 mol, preferably $1\times10^{-5}$ to 5 mol, more preferably $1\times10^{-4}$ to 1 mol per 1 mol of the monomers.

The amount of water for obtaining the polysiloxane by hydrolysis condensation of these monomers is preferably in the range of 0.1 to 50 mol per 1 mol of a hydrolysable substituent bonded to the monomers. If the amount is 50 mol or less, a reaction device does not become excessively large, therefore it is economical.

As an operation manner, the monomers are added to a catalyst aqueous solution to start hydrolysis condensation reaction. In the manner, an organic solvent may be added to the catalyst aqueous solution, the monomers may be diluted with an organic solvent, or both may be performed. The reaction temperature is preferably in the range of 0 to 100° C., and more preferably 5 to 80° C. A method for maintaining the temperature at 5 to 80° C. while the monomers are dropped, and then aging the mixture at 20 to 80° C. is preferable.

As the organic solvent that can be added to the base catalyst aqueous solution, or can dilute the monomers, the same solvents as those exemplified for the organic solvent that can be added to the acid catalyst aqueous solution are preferably used. The amount of the organic solvent to be used is preferably in the range of 0 to 1,000 mL, and particularly preferably 0 to 500 mL per 1 mol of the monomers. By using such an amount, a reaction vessel does not become excessively large, therefore it is economical.

Thereafter, if necessary, neutralization reaction of the catalyst is carried out, and alcohol produced by hydrolysis condensation reaction is removed under reduced pressure to obtain a reaction mixture aqueous solution. The amount of an acid substance to be used for neutralization is preferably 0.1 to 2 equivalent weight with respect to basic substance used as the catalyst. The acid substance may be any substance so long as it shows acidity in water.

Subsequently, it is preferable that by-products such as alcohol produced by hydrolysis condensation reaction be removed from the reaction mixture. The temperature for heating the reaction mixture and degree of vacuum may be the same temperature and degree of vacuum as in the case of using the acid catalyst.

Next, the base catalyst used for hydrolysis condensation may be removed from the reaction mixture. A method for removing the base catalyst may be to mix water and the polysiloxane, and then extract the polysiloxane by an organic solvent. As the organic solvent, the same solvent as those exemplified for the organic solvent used for removing the acid catalyst as mentioned above may be used.

Furthermore, a mixture of a water-soluble organic solvent and a slightly water-soluble organic solvent can also be used. As the mixture of a water-soluble organic solvent and a slightly water-soluble organic solvent, the same mixture as exemplified above for the mixture used for removing the acid catalyst may be used.

The mixing ratio of the water-soluble organic solvent and the slightly water-soluble organic solvent may be the same ratio as those used for removing the acid catalyst.

Subsequently, the reaction mixture may be washed with neutral water. The neutral water may be water called deionized water or ultrapure water. The amount of the water, the washing method, and the number of washing may be the same as in the case of using the acid catalyst.

Also, in the operation of water-washing, there is a case that a part of the polysiloxane escapes into a water layer, thereby substantially the same effect as fractionation operation is obtained. Therefore, the number of washing and the amount of water for washing may be appropriately determined in view of effects of catalyst removal and fractionation.

A final solvent is then added to the polysiloxane solution even when the base catalyst remains therein or has been removed therefrom, and solvent-exchange is thereby performed under reduced pressure to obtain a desired solution of the polysiloxane. The temperature and degree of vacuum during the solvent exchange, and final concentration of the polysiloxane solution may be the same in the case of using the acid catalyst.

Also, the final solution added to the polysiloxane solution may be the same as in the case of using the acid catalyst.

Moreover, a stabilizer may be added thereto like the case of using the acid catalyst.

As an alternative operation manner, water or a water-containing organic solvent may be added to the monomers or an organic solution of the monomers to start hydrolysis reaction. In the manner, the catalyst may be added to the monomers or the organic solution of the monomers, or may be added to the water or the water-containing organic solvent. The reaction temperature is preferably in the range of 0 to 100° C., and more preferably 10 to 80° C. A method for heating the mixture at 10 to 50° C. while water is dropped, and then increasing the temperature to 20 to 80° C. to age the mixture is preferable.

When the organic solvent is used, the same materials as in the case of using the acid catalyst may be used.

The molecular weight of the polysiloxane thus obtained can be adjusted not only by selecting monomers, but also controlling reaction conditions during polymerization. The weight average molecular weight of the polysiloxane is preferably 100,000 or less, more preferably in the range of 200 to 50,000, and much more preferably 300 to 30,000. If the weight average molecular weight is 100,000 or less, generation of foreign matters and coating spots can be suppressed.

Meanwhile, the above weight average molecular weight is obtained as data, in terms of polystyrene as a reference material, by means of gel-permeation chromatography (GPC) using refractive index (RI) detector as a detector and tetrahydrofuran as an eluent.

[Other Additives]

To improve stability of the composition for forming a resist under layer film of the present invention, a monovalent, divalent or more polyvalent organic acid having 1 to 30 carbon atoms is preferably added thereinto. Preferable examples of the organic acid include formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid, etc. Especially, oxalic acid, maleic acid, formic acid, acetic acid, propionic acid, citric acid, and the like are preferable. To keep stability, two or more kinds of these acids may be used as a mixture. The amount thereof to be added is preferably in the range of 0.001 to 25 parts by mass, more preferably 0.01 to 15 parts by mass, and much more preferably 0.1 to 5 parts by mass, based on 100 parts by mass of the polysiloxane contained in the composition.

Alternatively, the organic acid is preferably added such that pH of the composition becomes preferably 0≤pH≤7, more preferably 0.3≤pH≤6.5, and much more preferably 0.5≤pH≤6.

Moreover, water may be added to the composition for forming a resist under layer film of the present invention. When water is added thereinto, the polysiloxane is hydrated whereby improving a lithography performance. Water content in the solvent component of the composition is preferably more than 0% and less than 50% by mass, more preferably in the range of 0.3 to 30% by mass, and much more preferably 0.5 to 20% by mass.

The amount of all solvents including water is preferably in the range of 100 to 100,000 parts by mass, and more preferably 200 to 50,000 parts by mass, based on 100 parts by mass of the base polymer (polysiloxane). By adding in such an amount, lithography performance can be improved, and uniformity of the coated film does not tend to be deteriorated, thereby causing of eye holes can be suppressed.

A photo-acid generator may be added to the composition for forming a resist under layer film of the present invention. Illustrative examples of the photo-acid generator include a material described in paragraphs (0160) to (0179) of Japanese Patent Laid-Open Publication No. 2009-126940.

Also, a stabilizer may be added to the composition for forming a resist under layer film of the present invention to improve stability of the composition. The stabilizer may be exemplified by ether compounds such as monovalent, divalent, or more polyvalent alcohols having cyclic ether as a substituent. Illustrative examples thereof include those described in paragraphs (0180) to (0184) of Japanese Patent Laid-Open Publication No. 2009-126940.

Also, a surfactant may be added to the composition for forming a resist under layer film of the present invention, if necessary. Illustrative examples of the surfactant include those described in paragraph (0185) of Japanese Patent Laid-Open Publication No. 2009-126940.

As described above, the composition for forming a resist under layer film of the present invention can form a resist under layer film which can suppress reflection particularly in KrF exposure process, and has excellent adhesiveness to a resist pattern formed thereon and excellent dry etching selectivity between a resist pattern formed thereon and an organic under layer film or the like formed thereunder.

<Patterning Process>

The present invention provides a patterning process which includes the steps of: forming an organic under layer film on a body to be processed by using a coating type organic under layer film material; forming a resist under layer film on the organic under layer film by using the above-mentioned composition for forming a resist under layer film of the present invention; forming a resist pattern on the resist under layer film; transferring the pattern to the resist under layer film by dry etching using the resist pattern as a mask; transferring the pattern to the organic under layer film by dry etching using the resist under layer film to which the pattern has been transferred as a mask; and further transferring the pattern to the body to be processed by dry etching using the organic under layer film to which the pattern has been transferred as a mask.

Also, the present invention provides a patterning process which includes the steps of: forming an organic hard mask mainly comprising carbon on a body to be processed by a CVD method; forming a resist under layer film on the organic hard mask by using the above-mentioned composition for forming a resist under layer film of the present invention; forming a resist pattern on the resist under layer film; transferring the pattern to the resist under layer film by dry etching using the resist pattern as a mask; transferring the pattern to the organic hard mask by dry etching using the resist under layer film to which the pattern has been transferred as a mask; and further transferring the pattern to the body to be processed by dry etching using the organic hard mask to which the pattern has been transferred as a mask.

Here, as the body to be processed, a semiconductor apparatus substrate, a material in which any of a metal film, a metal carbide film, a metal oxide film, a metal nitride film, a metal oxycarbide film, and a metal oxynitride film is formed as a layer to be processed (a portion to be processed) on the semiconductor apparatus substrate, or the like may be used.

As the semiconductor substrate, a silicon substrate is generally used, but it is not particularly limited, and a material such as Si, amorphous silicon ($\alpha$-Si), p-Si, $SiO_2$, SiN, SiON, W, TiN, Al, etc., and different in the material from the layer to be processed may be used.

Examples of a metal constituting the body to be processed include silicon, titanium, tungsten, hafnium, zirconium, chromium, germanium, copper, aluminum, indium, gallium, arsenic, palladium, iron, tantalum, iridium, molybdenum, and an alloy thereof. The layer to be processed may be made of Si, $SiO_2$, SiN, SiON, SiOC, p-Si, $\alpha$-Si, TiN, BPSG, SOG, Cr, CrO, CrON, MoSi, W, W—Si, Al, Cu, Al—Si, or the like; various low dielectric constant (low-k) films, or etching stopper film thereof. The thickness of the layer is preferably in the range of 50 to 10,000 nm, and more preferably 100 to 5,000 nm.

In the patterning process of the present invention, an organic under layer film is formed on the body to be processed by using a coating type organic under layer film material, or an organic hard mask mainly comprising carbon is formed on the body to be processed by a CVD method.

As used herein, the term "coating type organic under layer film material" refers to a material capable of forming an organic under layer film by coating a solution of the material on the body to be processed by a spin-coating method or the like.

The coating type organic under layer film material preferably contains an anthracene skeleton. If the resist under layer film is formed by using the composition for forming a resist under layer film of the present invention on the organic under layer film containing an anthracene skeleton, reflection can be further suppressed.

The resist under layer film used in the patterning process of the present invention can be formed on the organic under layer film or on the organic hard mask by using a spin-coating method or the like, from the composition for forming a resist under layer film of the present invention, as well as a photoresist film. After spin coating, it is desired to be baked for evaporating the solvent, preventing from mixing with the resist upper layer film (photoresist film), and promoting cross-linking reaction. The baking temperature is preferably in the range of 50 to 500° C., and the heating time is preferably in the range of 10 to 300 seconds. Particularly preferable temperature range is 400° C. or less in order to reduce heat damage to the devices though it is depending on the structure of the devices to be fabricated.

Thus, if the resist under layer film is formed by using the composition for forming a resist under layer film of the present invention, a resist under layer film which can suppress reflection particularly in KrF exposure process, and has excellent adhesiveness to a resist pattern formed on the resist under layer film and excellent dry etching selectivity between the resist pattern (photoresist film) formed on the resist under layer film and the organic under layer film (or the organic hard mask) formed under the resist under layer film can be formed.

In the patterning process of the present invention, the resist pattern can be formed by a known method such as photolithography using a resist composition. For example, the resist pattern can be formed by forming a photoresist film on the resist under layer film from a chemically amplified resist composition, exposing the formed photoresist film to a high-energy beam after heat treatment, and then performing development. The development may be performed by positive development in which an exposed portion of the photoresist film is dissolved by using an alkaline developer, or by negative development in which an unexposed portion of the photoresist film is dissolved by using a developer consisting of an organic solvent.

In the patterning process of the present invention, the resist composition used in the above-mentioned lithography for forming the resist pattern is not particularly limited so long as it is a chemical amplified resist composition, and can form a pattern by positive development using an alkaline developer, or negative development using a developer consisting of an organic solvent.

As the lithography method using a high-energy beam, a lithography method using light having a wavelength of 300 nm or less is preferably used, and exposure process by KrF excimer laser beam (KrF exposure process) is particularly preferable. In this case, a conventional resist composition for KrF excimer laser is preferably used for an upper layer photoresist film. Alternatively, ArF exposure can also be applied.

Other methods for forming the resist pattern include a directed self-assembly method (DSA method) and a nano-imprinting lithography method.

By using such a method, a fine pattern can be formed on the substrate with high precision.

As mentioned above, the quaternary ammonium salt compound of the present invention can form a resist under layer film that can suppress reflection particularly in KrF exposure process, and exhibits excellent adhesiveness to a resist pattern formed thereon and high dry etching selectivity to both of the resist pattern formed thereon and an organic under layer film (or an organic hard mask) formed thereunder, by adding the quaternary ammonium salt compound, for example, as a thermal crosslinking accelerator to a composition for forming a resist under layer film containing a polysiloxane. Accordingly, when the formed resist pattern is successively transferred to the resist under layer film and the organic under layer film (or the organic hard mask) by dry etching process, the pattern can be transferred with good pattern profile. In this way, the pattern formed to the upper layer resist can be finally transferred to a body to be processed with high precision.

EXAMPLES

Hereinafter, the present invention will be specifically described with reference to Synthesis Examples, Examples and Comparative Examples, but it is not restricted thereto.

[Synthesis of Quaternary Ammonium Salt Compounds]

The quaternary ammonium salt compounds of the present invention represented by the formula (A-1) were synthesized in a manner shown below (Synthesis Examples 1-1 to 1-8).

Synthesis Example 1-1

Synthesis of (9-anthracenyl-methyl)benzyldimethylammonium chloride (S1)

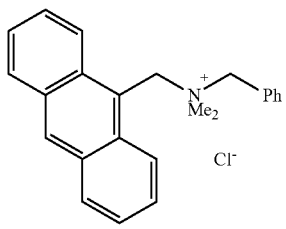

S1

5.0 g of 9-chloromethyl anthracene was dissolved in 15 g of N-methyl pyrrolidone. 3.6 g of benzyldimethyl-amine was added thereto, followed by stirring at 50° C. for 4 hours. Then, 50 g of 4-methyl-2-pentanone was added thereto, and allowed to cool for 16 hours. The resulting solid was collected by filtration, washed with 4-methyl-2-pentanone, and dried under reduced pressure at 60° C., thereby 7.8 g of (9-anthracenylmethyl)benzyl-dimethylammonium chloride was obtained.

Incidentally, the obtained compound was identified as (9-anthracenylmethyl)benzyldimethylammonium chloride (S1) by analysis using MALDI-TOF-MS, IR, $^1$H-NMR, and $^{13}$C-NMR.

MALDI-TOF-MS (DCTB/CHCl$_3$): (+)191.1, 326.2, (−)35.0

IR(D-ATR): ν=3083, 3054, 3023, 2995, 2968, 1624, 1481, 1454, 1439, 1413, 1351, 1340, 1261, 1222, 1050, 1039, 991, 982, 972, 931, 893, 854, 806, 769, 747, 735, 708, 652, 601 cm$^{-1}$ $^1$H-NMR (500 MHz in DMSO-d6): δ=2.81 (6H, s), 5.18 (2H, t, J=3 Hz), 5.98 (2H, s), 7.45-7.53 (3H, m), 7.59 (2H, dd, J=8, 7 Hz), 7.65-7.72 (4H, m), 8.20 (2H, d, J=9 Hz), 8.90 (3H, m)

$^{13}$C-NMR (125 MHz in DMSO-d6): δ=48.20, 59.02, 66.55, 119.32, 125.08, 125.33, 127.51, 128.43, 128.77, 129.43, 130.18, 130.99, 131.95, 133.03, 133.36

Synthesis Example 1-2

Synthesis of (9-anthracenyl-methyl)benzyldimethylammonium nitrate (S2)

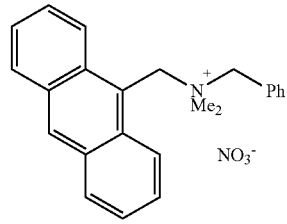

S2

A mixture of 3.6 g of (9-anthracenylmethyl)benzyl-dimethylammonium chloride, 2.2 g of silver(I) nitrate, and 20 g of methanol was stirred at 60° C. for 20 hours. The insoluble matter was collected by filtration, and concentrated under reduced pressure, thereby 3.6 g of (9-anthracenylmethyl)benzyldimethylammonium nitrate was obtained.

Incidentally, the obtained compound was identified as (9-anthracenylmethyl)benzyldimethylammonium nitrate (S2) by analysis using MALDI-TOF-MS, IR, $^1$H-NMR and $^{13}$C-NMR.

MALDI-TOF-MS (DCTB/CHCl$_3$): (+)191.2, 326.2, (−)62.0

IR(D-ATR): ν=3037, 1746, 1707, 1625, 1504, 1483, 1446, 1415, 1357, 1329, 1260, 1183, 1160, 1041, 989, 956, 928, 895, 856, 810, 769, 741, 728, 709, 655, 603 cm$^{-1}$ $^1$H-NMR (500 MHz in DMSO-d6): δ=2.78 (6H, s), 4.89 (2H, s), 5.82 (2H, s), 7.45-7.55 (3H, m), 7.60-7.65 (4H, m), 7.70-7.75 (2H, m), 8.23 (2H, d, J=8 Hz), 8.66 (2H, d, J=10 Hz), 8.93 (1H, s)

$^{13}$C-NMR (125 MHz in DMSO-d6): δ=48.50, 59.26, 67.21, 119.07, 124.54, 125.39, 127.66, 128.09, 128.94, 129.61, 130.36, 131.05, 132.11, 132.96, 133.30

Synthesis Example 1-3

Synthesis of [3-(9-anthracenyl-carbonyloxy)propyl]triethylammonium chloride (S3)

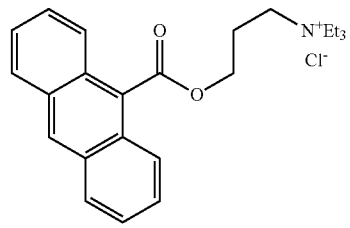

S3

A mixture of 11 g of 3-chloropropyl 9-anthracene-carboxylate, 32 g of triethylamine, and 30 g of acetonitrile was stirred at 140° C. for 3.5 hours in an autoclave. The reaction solution was concentrated, and then purified by silica gel column chromatography, thereby 2.3 g of [3-(9-anthracenylcarbonyloxy)propyl]-triethylammonium chloride was obtained.

Incidentally, the obtained compound was identified as [3-(9-anthracenylcarbonyloxy)propyl]triethylammonium chloride (S3) by analysis using MALDI-TOF-MS, $^1$H-NMR, and $^{13}$C-NMR.

MALDI-TOF-MS (DCTB/CHCl₃): (+)364.2, (−)35.0

¹H-NMR (600 MHz in DMSO-d6): δ=1.11 (9H, t, J=7 Hz), 2.20 (2H, m), 3.26 (6H, q, J=7 Hz), 3.32 (2H, m), 4.69 (2H, t, J=6 Hz), 7.59 (2H, br.t, J=8 Hz), 7.65 (2H, br.t, J=9 Hz), 8.04 (2H, br.d, 8 Hz), 8.17 (2H, br.d, 9 Hz), 8.80 (1H, s)

¹³C-NMR (150 MHz in DMSO-d6): δ=7.11, 21.01, 52.10, 53.25, 54.93, 124.58, 125.79, 127.21, 127.48, 127.52, 128.66, 129.42, 130.38, 168.45

Synthesis Example 1-4

Synthesis of [3-(9-anthracenyl-carbonyloxy)propyl]triethylammonium nitrate (S4)

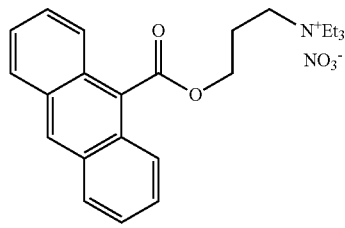

S4

A mixture of 2.3 g of [3-(9-anthracenyl-carbonyloxy)propyl]triethylammonium chloride, 1.4 g of silver(I) nitrate, and 10 g of tert-butyl alcohol was stirred at 80° C. for 40 hours. The insoluble matter was collected by filtration, concentrated under reduced pressure, and then purified by silica gel column chromatography, thereby 1.8 g of [3-(9-anthracenyl-carbonyloxy)propyl]triethylammonium nitrate was obtained.

Incidentally, the obtained compound was identified as [3-(9-anthracenylcarbonyloxy)propyl]triethylammonium nitrate (S4) by analysis using MALDI-TOF-MS, IR, ¹H-NMR, and ¹³C-NMR.

MALDI-TOF-MS (DCTB/CHCl₃): (+)364.2, (−)62.0

IR(D-ATR): ν=2987, 1721, 1625, 1523, 1448, 1397, 1341, 1264, 1206, 1174, 1153, 1039, 1015, 862, 826, 796, 746 cm⁻¹

¹H-NMR (500 MHz in DMSO-d6): δ=1.10 (9H, br.t, J=7 Hz), 2.19 (2H, m), 3.21-3.31 (8H, m), 4.67 (2H, br.t, J=6 Hz), 7.59 (2H, m), 7.65 (2H, m), 8.04 (2H, br.d, 9 Hz), 8.17 (2H, br.d, 9 Hz), 8.80 (1H, s)

¹³C-NMR (125 MHz in DMSO-d6): δ=7.07, 20.97, 52.08, 53.24, 62.75, 124.63, 125.86, 127.24, 127.53, 127.56, 128.71, 129.47, 130.43, 168.51

Synthesis Example 1-5

Synthesis of (9-anthracenyl-methoxycarbonylmethyl)trimethylammonium chloride (S5)

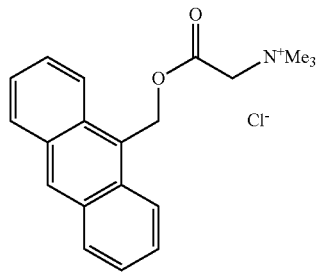

S5

A mixture of 2.5 g of betaine, 5.0 g of 9-chloromethyl anthracene, and 25 g of acetonitrile was stirred at 90° C. for 5 hours. 75 mL of 4-methyl-2-pentanone was added thereto, and allowed to cool. The resulting crystal was then collected by filtration, washed with 4-methyl-2-pentanone, and dried under reduced pressure at 50° C., thereby 5.8 g of (9-anthracenylmethoxycarbonylmethyl)trimethylammonium chloride was obtained.

Incidentally, the obtained compound was identified as (9-anthracenylmethoxycarbonylmethyl)trimethylammonium chloride (S5) by analysis using MALDI-TOF-MS, IR, ¹H-NMR, and ¹³C-NMR.

MALDI-TOF-MS (DCTB/CHCl₃): (+)308.2, (−)35.0

IR(D-ATR): ν=3016, 2952, 1742, 1719, 1625, 1482, 1463, 1403, 1259, 1196, 1143, 1121, 1046, 1014, 998, 958, 931, 882, 867, 742, 733, 702, 638, 600 cm⁻¹

¹H-NMR (600 MHz in DMSO-d6): δ=3.27 (9H, s), 4.57 (2H, s), 6.29 (2H, s), 7.57 (2H, m), 7.65 (2H, m), 8.15 (2H, d, J=8 Hz), 8.40 (2H, d, J=8 Hz), 8.74 (1H, s)

¹³C-NMR (150 MHz in DMSO-d6): δ=53.01, 60.09, 62.42, 123.09, 124.99, 125.35, 126.99, 129.02, 129.45, 130.56, 130.83, 164.99

Synthesis Example 1-6

Synthesis of (9-anthracenyl-methoxycarbonylmethyl)trimethylammonium nitrate (S6)

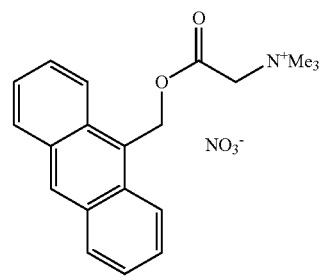

S6

A mixture of 3.0 g of (9-anthracenylmethoxy-carbonylmethyl)trimethylammonium chloride, 1.6 g of silver(I) nitrate, and 15 g of tert-butyl alcohol was stirred at 80° C. for 6 hours. The resulting solid was collected by filtration, the target compound was then extracted from the solid by using methylene chloride, and concentrated. Then, 4-methyl-2-pentanone was added thereto, and the resulting mixture was stirred. The resulting solid was then collected by filtration, and dried under reduced pressure, thereby 1.8 g of (9-anthracenylmethoxycarbonylmethyl)trimethylammonium nitrate was obtained.

Incidentally, the obtained compound was identified as (9-anthracenylmethoxycarbonylmethyl)trimethylammonium nitrate (S6) by analysis using IR, ¹H-NMR, and ¹³C-NMR.

IR(D-ATR): ν=3034, 2981, 1748, 1625, 1492, 1478, 1463, 1407, 1359, 1326, 1269, 1258, 1192, 1182, 1163, 1135, 1055, 1040, 1007, 997, 958, 932, 906, 894, 885, 868, 790, 765, 733, 702 cm⁻¹

¹H-NMR (600 MHz in DMSO-d6): δ=3.24 (9H, s), 4.45 (2H, s), 6.30 (2H, s), 7.57 (2H, m), 7.65 (2H, m), 8.15 (2H, d, J=9 Hz), 8.40 (2H, dd, J=9, 1 Hz), 8.74 (1H, s)

¹³C-NMR (150 MHz in DMSO-d6): δ=53.16, 60.12, 62.56, 123.90, 124.96, 125.36, 126.99, 129.02, 129.46, 130.57, 130.84, 164.88

Synthesis Example 1-7

Synthesis of
(9-anthracenyl-methyl)trimethylammonium
benzoate (S7)

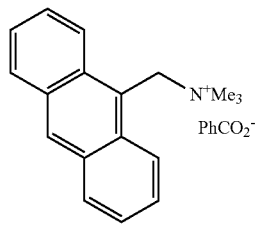

S7

10.0 g of 9-chloromethyl-anthracene was dissolved in 40 g of N-methylpyrrolidone. Thereto, 30 g of trimethylamine (13% by weight tetrahydrofuran solution) was added over 40 minutes, followed by stirring at 50° C. for 3 hours. Then, 70 g of 4-methyl-2-pentanone was added thereto, and allowed to cool for 16 hours. The resulting solid was collected by filtration, washed with 4-methyl-2-pentanone, and then dried under reduced pressure at 50° C., thereby 12.5 g of (9-anthracenyl-methyl)trimethylammonium chloride was obtained.

To a mixture of 1.47 g of benzoic acid and 16 g of acetonitrile were added 1.39 g of silver(I) oxide, and then 3.43 g of (9-anthracenylmethyl)trimethylammonium chloride, and the resulting mixture was stirred at room temperature for 20 hours. Subsequently, methanol was added thereto, and the insoluble matter was collected by filtration, and concentrated under reduced pressure. Diisopropyl ether was then added thereto, the precipitated crystal was collected by filtration, and dried under reduced pressure, thereby 4.26 g of (9-anthracenylmethyl)trimethylammonium benzoate was obtained.

Incidentally, the obtained compound was identified as (9-anthracenylmethyl)trimethylammonium benzoate (S7) by analysis using LC-MS, IR, $^1$H-NMR, and $^{13}$C-NMR.

LC-MS(ESI): (+)250, (−)121
IR(D-ATR): ν=3017, 1622, 1605, 1564, 1492, 1460, 1449, 1364, 1261, 1188, 1162, 1064, 1049, 1021, 972, 946, 900, 876, 868, 825, 797, 750, 735, 719, 670, 634, 602 cm$^{-1}$
$^1$H-NMR (500 MHz in DMSO-d6): δ=3.13 (9H, s), 5.78 (2H, s), 7.23 (3H, m), 7.58 (2H, dd, J=9, 7 Hz), 7.65 (2H, m), 7.87 (2H, m), 8.19 (2H, d, J=9 Hz), 8.81 (2H, d, J=9 Hz), 8.88 (1H, s)
$^{13}$C-NMR (125 MHz in DMSO-d6): δ=52.70, 58.76, 119.85, 124.96, 125.35, 126.89, 127.46, 128.01, 128.93, 129.40, 130.97, 131.74, 132.82, 141.78, 168.31

Synthesis Example 1-8

Synthesis of
(9-anthracenyl-methyl)trimethylammonium
trifluoroacetate (S8)

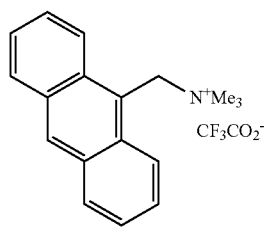

S8

To a mixture of 1.20 g of trifluoroacetic acid and 16 g of acetonitrile were added 1.16 g of silver(I) oxide, and then 2.86 g of (9-anthracenylmethyl)trimethylammonium chloride, and the resulting mixture was stirred at room temperature for 20 hours. Subsequently, methanol was added thereto, and the insoluble matter was collected by filtration, and concentrated under reduced pressure. Diisopropyl ether was then added thereto, the precipitated crystal was collected by filtration, and dried under reduced pressure, thereby 3.37 g of (9-anthracenylmethyl)trimethylammonium trifluoroacetate was obtained.

Incidentally, the obtained compound was identified as (9-anthracenylmethyl)trimethylammonium trifluoroacetate (S8) by analysis using LC-MS, $^1$H-NMR, $^{13}$C-NMR, and $^{19}$F-NMR.

LC-MS(ESI): (+)250, (−)113
IR(D-ATR): ν=3032, 1682, 1667, 1626, 1526, 1507, 1496, 1481, 1450, 1413, 1120, 1167, 1119, 976, 947, 924, 878, 823, 802, 754, 736, 715, 648, 636, 602 cm$^{-1}$
$^1$H-NMR (500 MHz in DMSO-d6): δ=3.09 (9H, s), 5.69 (2H, s), 7.60 (2H, dd, J=8, 7 Hz), 7.70 (2H, m), 8.21 (2H, d, J=9 Hz), 8.72 (2H, d, J=9 Hz), 8.90 (1H, s)
$^{13}$C-NMR (125 MHz in DMSO-d6): δ=52.73, 58.83, 117.48 (q, J=300 Hz), 119.62, 124.74, 125.35, 127.49, 129.45, 130.96, 131.80, 132.77, 157.91 (q, J=30 Hz)
$^{19}$F-NMR (470 MHz in DMSO-d6): δ=−74.79 (3F, s)

[Synthesis of Polysiloxanes]

The polysiloxanes represented by the formula (B-1) were synthesized in a manner shown below (Synthesis Examples 2-1 to 2-3).

Synthesis Example 2-1

Synthesis of Polysiloxane 1

To a mixture of 260 g of ethanol, 0.2 g of methanesulfonic acid, and 260 g of deionized water was added a mixture of 34.1 g of methyl trimethoxy silane and 52.2 g of tetraethoxy silane, and the resulting mixture was maintained at 40° C. for 12 hours to carry out hydrolysis condensation. After completion of the reaction, 300 g of propylene glycol ethyl ether (PGEE) was added thereto, and a by-produced alcohol and excess water were distilled off under reduced pressure, thereby 260 g of a PGEE solution containing Polysiloxane 1 was obtained (compound concentration: 11.2%). When the molecular weight of Polysiloxane 1 in terms of polystyrene was measured, it was Mw=2,300.

Synthesis Example 2-2

Synthesis of Polysiloxane 2

To a mixture of 260 g of ethanol, 0.2 g of methanesulfonic acid, and 260 g of deionized water was added a mixture of 5.0 g of phenyl trimethoxy silane and 99.2 g of tetraethoxy silane, and the resulting mixture was maintained at 40° C. for 12 hours to carry out hydrolysis condensation. After completion of the reaction, 300 g of propylene glycol ethyl ether (PGEE) was added thereto, and a by-produced alcohol and excess water were distilled off under reduced pressure, thereby 290 g of a PGEE solution containing Polysiloxane 2 was obtained (compound concentration: 10.1%). When the molecular weight of Polysiloxane 2 in terms of polystyrene was measured, it was Mw=1,900.

Synthesis Example 2-3

Synthesis of Polysiloxane 3

To a mixture of 260 g of ethanol, 0.2 g of methanesulfonic acid, and 260 g of deionized water was added 68.1 g of methyl trimethoxy silane, and the resulting mixture was maintained at 40° C. for 12 hours to carry out hydrolysis condensation. After completion of the reaction, 300 g of propylene glycol ethyl ether (PGEE) was added thereto, and a by-produced alcohol and excess water were distilled off under reduced pressure, thereby 310 g of a PGEE solution containing Polysiloxane 3 was obtained (compound concentration: 10.1%). When the molecular weight of Polysiloxane 3 in terms of polystyrene was measured, it was Mw=2,200.

Examples and Comparative Examples

Polysiloxanes 1 to 3 obtained in the above Synthesis Examples 2-1 to 2-3, the quaternary ammonium salt compounds (S1 to S8) obtained in the above Synthesis Examples 1-1 to 1-8 as a thermal crosslinking accelerator, solvents, and additive ($H_2O$) were mixed with the ratios shown in Table 1, and the respective mixtures were filtered through 0.1 μm of a filter made of a fluorine resin to prepare the respective compositions for forming a resist under layer film, which were named Sols. 1 to 19.

TABLE 1

| No. | Polysiloxane (parts by mass) | Thermal crosslinking accelerator (parts by mass) | Solvent (parts by mass) | Additive (parts by mass) |
| --- | --- | --- | --- | --- |
| Sol. 1 | 1 (6.0) | S1 (0.3) | PGEE (140) | $H_2O$ (10) |
| Sol. 2 | 1 (6.0) | S2 (0.3) | PGEE (140) | $H_2O$ (10) |
| Sol. 3 | 1 (6.0) | S3 (0.3) | PGEE (140) | $H_2O$ (10) |
| Sol. 4 | 1 (6.0) | S4 (0.3) | PGEE (140) | $H_2O$ (10) |
| Sol. 5 | 1 (6.0) | S5 (0.3) | PGEE (140) | $H_2O$ (10) |
| Sol. 6 | 1 (6.0) | S6 (0.3) | PGEE (140) | $H_2O$ (10) |
| Sol. 7 | 1 (6.0) | S7 (0.3) | PGEE (140) | $H_2O$ (10) |
| Sol. 8 | 1 (6.0) | S8 (0.3) | PGEE (140) | $H_2O$ (10) |
| Sol. 9 | 2 (5.4) 3 (0.6) | S1 (0.3) | PGEE (140) | $H_2O$ (10) |
| Sol. 10 | 2 (5.4) 3 (0.6) | S2 (0.3) | PGEE (140) | $H_2O$ (10) |
| Sol. 11 | 2 (5.4) 3 (0.6) | S3 (0.3) | PGEE (140) | $H_2O$ (10) |
| Sol. 12 | 2 (5.4) 3 (0.6) | S4 (0.3) | PGEE (140) | $H_2O$ (10) |
| Sol. 13 | 2 (5.4) 3 (0.6) | S5 (0.3) | PGEE (140) | $H_2O$ (10) |
| Sol. 14 | 2 (5.4) 3 (0.6) | S6 (0.3) | PGEE (140) | $H_2O$ (10) |
| Sol. 15 | 2 (5.4) 3 (0.6) | S7 (0.3) | PGEE (140) | $H_2O$ (10) |
| Sol. 16 | 2 (5.4) 3 (0.6) | S8 (0.3) | PGEE (140) | $H_2O$ (10) |
| Sol. 17 | 1 (6.0) | TMBMA (0.3) | PGEE (140) | $H_2O$ (10) |
| Sol. 18 | 1 (6.0) | None | PGEE (140) | $H_2O$ (10) |
| Sol. 19 | 2 (5.4) 3 (0.6) | None | PGEE (140) | $H_2O$ (10) |

TMBMA: Mono(benzyltrimethylammonium) maleate (Evaluation of Optical Characteristics)

Sols. 1 to 19 were each spin-coated, and heated at 200° C. for 60 seconds to prepare a polysiloxane-containing film with a film thickness of 80 nm (Films 1 to 19). Then, optical constants (refractive index: n, extinction coefficient: k, and reflection) of Films 1 to 19 at wavelength of 248 nm were measured by a variable angle spectroscopic ellipsometer (VUV-VASE manufactured by J.A. Woollam co., Inc.). The results are shown in Table 2.

TABLE 2

| | Film | Refractive index: n | Extinction coefficient: k | Reflection |
| --- | --- | --- | --- | --- |
| Example 1-1 | Film 1 | 1.46 | 0.08 | 1% or less |
| Example 1-2 | Film 2 | 1.46 | 0.08 | 1% or less |
| Example 1-3 | Film 3 | 1.46 | 0.07 | 1% or less |
| Example 1-4 | Film 4 | 1.46 | 0.06 | 1% or less |
| Example 1-5 | Film 5 | 1.46 | 0.07 | 1% or less |
| Example 1-6 | Film 6 | 1.46 | 0.06 | 1% or less |
| Example 1-7 | Film 7 | 1.47 | 0.06 | 1% or less |
| Example 1-8 | Film 8 | 1.47 | 0.05 | 1% or less |
| Example 1-9 | Film 9 | 1.46 | 0.08 | 1% or less |
| Example 1-10 | Film 10 | 1.46 | 0.08 | 1% or less |
| Example 1-11 | Film 11 | 1.46 | 0.07 | 1% or less |
| Example 1-12 | Film 12 | 1.46 | 0.07 | 1% or less |
| Example 1-13 | Film 13 | 1.46 | 0.06 | 1% or less |
| Example 1-14 | Film 14 | 1.47 | 0.06 | 1% or less |
| Example 1-15 | Film 15 | 1.47 | 0.06 | 1% or less |
| Example 1-16 | Film 16 | 1.47 | 0.05 | 1% or less |
| Comparative Example 1-1 | Film 17 | 1.51 | 0.01 | 1.5% or more |
| Comparative Example 1-2 | Film 18 | 1.52 | 0.00 | 1.5% or more |
| Comparative Example 1-3 | Film 19 | 1.52 | 0.00 | 1.5% or more |

As shown in Table 2, as compared with Film 17 formed by using Sol. 17 including the conventional thermal crosslinking accelerator, and Films 18 and 19 formed by using Sols. 18 and 19 including no thermal crosslinking accelerator, Films 1 to 16 formed by using Sols. 1 to 16 including the quaternary ammonium salt compound of the present invention as a thermal crosslinking accelerator showed suppressed refractive index and good extinct coefficient, and reflection of KrF laser was suppressed to 1% or less.

(Patterning Test)

A composition for forming a spin-on carbon film ODL-69 (Carbon content: 86% by mass) available from Shin-Etsu Chemical Co., Ltd., was coated on a silicon wafer with a film thickness of 2.0 μm, and heated at 300° C. for 60 seconds to form an organic under layer film. The compositions for forming a resist under layer film, Sols. 1 to 19, were each coated thereon, and heated at 200° C. for 60 seconds to form resist under layer films, Films 1 to 19, with a film thickness of 80 nm, respectively.

Subsequently, the KrF resist solution (PR-1) described in Table 3 was coated on Films 1 to 19, and baked at 100° C. for 90 seconds to form a photoresist film having a film thickness of 250 nm.

Next, these were exposed by an KrF liquid immersion exposure apparatus (NSR-S206D manufactured by Nikon Corporation, NA-0.68), baked at 110° C. for 60 seconds (PEB), and developed by a 2.38% by mass tetramethylammonium hydroxide (TMAH) aqueous solution to obtain 130 nm line and space pattern. A cross-sectional shape of the wafer thus obtained was observed by an electron microscope (S-9380) manufactured by Hitachi Ltd. The results are shown in Table 4.

TABLE 3

| | Polymer (parts by mass) | Acid generator (parts by mass) | Base (parts by mass) | Surfactant (parts by mass) | Solvent A (parts by mass) | Solvent B (parts by mass) |
| --- | --- | --- | --- | --- | --- | --- |
| PR-1 | KrF resist polymer (80) | PAG1 (1) PAG2 (2) | Base (0.2) | FC-4430 (0.5) | PGMEA (130) | Ethyl lactate (130) |

TABLE 3-continued

| Polymer (parts by mass) | Acid generator (parts by mass) | Base (parts by mass) | Surfactant (parts by mass) | Solvent A (parts by mass) | Solvent B (parts by mass) |
|---|---|---|---|---|---|

KrF resist polymer:
Molecular weight (Mw) = 15,000
Dispersity (Mw/Mn) = 1.98

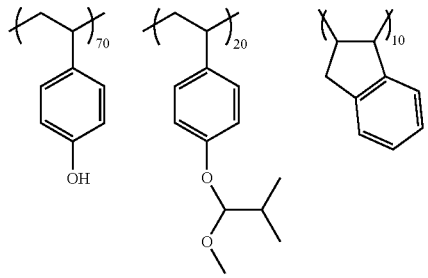

PAG1 (acid generator): (4-butoxyphenyl)diphenylsulfonium 10-camphorsulfonate
PAG2 (acid generator): bis(cyclohexylsulfonyl) diazomethane
Base (basic compound): tris(2-methoxyethyl)amine
Surfactant: FC-4430 (produced by Sumitomo 3M Inc.)
Solvent A: propylene glycol methyl ether acetate (PGMEA)
Solvent B: ethyl lactate

TABLE 4

| | Film | Pattern Profile |
|---|---|---|
| Example 2-1 | Film 1 | Rectangular |
| Example 2-2 | Film 2 | Rectangular |
| Example 2-3 | Film 3 | Rectangular |
| Example 2-4 | Film 4 | Rectangular |
| Example 2-5 | Film 5 | Rectangular |
| Example 2-6 | Film 6 | Rectangular |
| Example 2-7 | Film 7 | Rectangular |
| Example 2-8 | Film 8 | Rectangular |
| Example 2-9 | Film 9 | Rectangular |
| Example 2-10 | Film 10 | Rectangular |
| Example 2-11 | Film 11 | Rectangular |
| Example 2-12 | Film 12 | Rectangular |
| Example 2-13 | Film 13 | Rectangular |
| Example 2-14 | Film 14 | Rectangular |
| Example 2-15 | Film 15 | Rectangular |
| Example 2-16 | Film 16 | Rectangular |
| Comparative Example 2-1 | Film 17 | Tapered |
| Comparative Example 2-2 | Film 18 | Tapered |
| Comparative Example 2-3 | Film 19 | Tapered |

As shown in Table 4, when a pattern was formed on the resist under layer film formed by using Sol. 17 including the conventional thermal crosslinking accelerator, and Sols. 18 and 19 including no thermal crosslinking accelerator, the cross-sectional shapes of the obtained pattern was tapered. In contrast, when a pattern was formed on the resist under layer film formed by using Sols. 1 to 16 including the quaternary ammonium salt compound of the present invention as a thermal crosslinking accelerator, the cross-sectional shapes of the obtained patterns was rectangular.

From the results mentioned above, it could be clarified that when a pattern is formed by using the composition for forming a resist under layer film including the quaternary ammonium salt compound of the present invention, reflection in KrF exposure process can be suppressed, and a rectangular pattern can be formed.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A quaternary ammonium salt compound represented by the following formula (A-1),

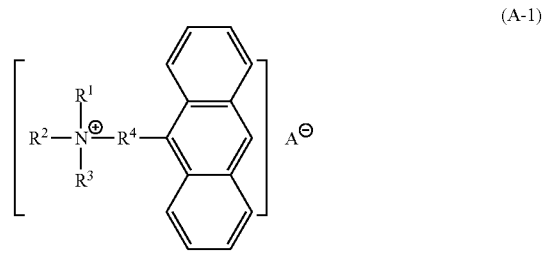

wherein, $R^1$, $R^2$, and $R^3$ each represent a linear, branched or cyclic alkyl group or alkenyl group having 1 to 12 carbon atoms, an aryl group having 6 to 20 carbon atoms, or an aralkyl group having 7 to 12 carbon atoms, a part or all of hydrogen atoms in these groups may be substituted by a hydroxyl group(s), an alkoxy group(s), or a halogen atom(s), and these groups may include one or more of a carbonyl group and an ester bond; $R^4$ represents a single bond, a linear, branched or cyclic alkylene group or alkenylene group having 1 to 12 carbon atoms, an arylene group having 6 to 20 carbon atoms, or an aralkylene group having 7 to 12 carbon atoms, a part or all of hydrogen atoms in these groups may be substituted by an alkoxy group(s) or a halogen atom(s), each of these groups of $R^4$ include an ester bond and may optionally include one or more of an ether bond, a carbonyl group, and an amide bond; and $A^-$ represents a non-nucleophilic counter ion.

2. A composition for forming a resist under layer film which comprises the quaternary ammonium salt compound according to claim 1 and a polysiloxane.

3. The composition for forming a resist under layer film according to claim 2, wherein the polysiloxane includes one or more members selected from a compound represented by the following formula (B-1), a hydrolysate of the compound, a condensate of the compound, and a hydrolysis condensate of the compound, $$R^{1B}{}_{B1}R^{2B}{}_{B2}R^{3B}{}_{B3}Si(OR^{OB})_{(4-B1-B2-B3)} \qquad \text{(B-1)}$$

wherein, $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \leq B1+B2+B3 \leq 3$.

4. A patterning process which comprises the steps of:
forming an organic under layer film on a body to be processed by using a coating type organic under layer film material;
forming a resist under layer film on the organic under layer film by using the composition for forming a resist under layer film according to claim 2;
forming a resist pattern on the resist under layer film;
transferring the pattern to the resist under layer film by dry etching using the resist pattern as a mask;
transferring the pattern to the organic under layer film by dry etching using the resist under layer film to which the pattern has been transferred as a mask; and further transferring the pattern to the body to be processed by dry etching using the organic under layer film to which the pattern has been transferred as a mask.

5. A patterning process which comprises the steps of:
forming an organic under layer film on a body to be processed by using a coating type organic under layer film material;
forming a resist under layer film on the organic under layer film by using the composition for forming a resist under layer film according to claim 3;
forming a resist pattern on the resist under layer film;
transferring the pattern to the resist under layer film by dry etching using the resist pattern as a mask;
transferring the pattern to the organic under layer film by dry etching using the resist under layer film to which the pattern has been transferred as a mask; and further
transferring the pattern to the body to be processed by dry etching using the organic under layer film to which the pattern has been transferred as a mask.

6. The patterning process according to claim 4, wherein the coating type organic under layer film material contains an anthracene skeleton.

7. The patterning process according to claim 5, wherein the coating type organic under layer film material contains an anthracene skeleton.

8. A patterning process which comprises the steps of:
forming an organic hard mask mainly comprising carbon on a body to be processed by a CVD method;
forming a resist under layer film on the organic hard mask by using the composition for forming a resist under layer film according to claim 2;
forming a resist pattern on the resist under layer film;
transferring the pattern to the resist under layer film by dry etching using the resist pattern as a mask;
transferring the pattern to the organic hard mask by dry etching using the resist under layer film to which the pattern has been transferred as a mask; and further
transferring the pattern to the body to be processed by dry etching using the organic hard mask to which the pattern has been transferred as a mask.

9. A patterning process which comprises the steps of:
forming an organic hard mask mainly comprising carbon on a body to be processed by a CVD method;
forming a resist under layer film on the organic hard mask by using the composition for forming a resist under layer film according to claim 3;
forming a resist pattern on the resist under layer film;
transferring the pattern to the resist under layer film by dry etching using the resist pattern as a mask;
transferring the pattern to the organic hard mask by dry etching using the resist under layer film to which the pattern has been transferred as a mask; and further
transferring the pattern to the body to be processed by dry etching using the organic hard mask to which the pattern has been transferred as a mask.

10. The patterning process according to claim 4, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

11. The patterning process according to claim 5, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

12. The patterning process according to claim 6, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

13. The patterning process according to claim 7, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

14. The patterning process according to claim 8, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

15. The patterning process according to claim 9, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

16. The patterning process according to claim 10, wherein a metal constituting the body to be processed comprises silicon, titanium, tungsten, hafnium, zirconium, chromium, germanium, copper, aluminum, indium, gallium, arsenic, palladium, iron, tantalum, iridium, molybdenum, or an alloy thereof.

17. The patterning process according to claim 11, wherein a metal constituting the body to be processed comprises silicon, titanium, tungsten, hafnium, zirconium, chromium, germanium, copper, aluminum, indium, gallium, arsenic, palladium, iron, tantalum, iridium, molybdenum, or an alloy thereof.

18. The patterning process according to claim 12, wherein a metal constituting the body to be processed comprises silicon, titanium, tungsten, hafnium, zirconium, chromium, germanium, copper, aluminum, indium, gallium, arsenic, palladium, iron, tantalum, iridium, molybdenum, or an alloy thereof.

19. The patterning process according to claim 13, wherein a metal constituting the body to be processed comprises silicon, titanium, tungsten, hafnium, zirconium, chromium, germanium, copper, aluminum, indium, gallium, arsenic, palladium, iron, tantalum, iridium, molybdenum, or an alloy thereof.

20. The patterning process according to claim 14, wherein a metal constituting the body to be processed comprises silicon, titanium, tungsten, hafnium, zirconium, chromium, germanium, copper, aluminum, indium, gallium, arsenic, palladium, iron, tantalum, iridium, molybdenum, or an alloy thereof.

* * * * *